US009611455B2

(12) United States Patent
Wagner et al.

(10) Patent No.: US 9,611,455 B2
(45) Date of Patent: Apr. 4, 2017

(54) ADAPTED LEPIDOPTERAN INSECT CELLS FOR THE PRODUCTION OF RECOMBINANT PROTEINS

(71) Applicant: Merck Sharp & Dohme Corp., Rahway, NJ (US)

(72) Inventors: James M. Wagner, Harleysville, PA (US); Shyamsundar Subramanian, Landsale, PA (US); David Pajerowski, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/775,154

(22) PCT Filed: Mar. 13, 2014

(86) PCT No.: PCT/US2014/025277
§ 371 (c)(1),
(2) Date: Sep. 11, 2015

(87) PCT Pub. No.: WO2014/159831
PCT Pub. Date: Oct. 2, 2014

(65) Prior Publication Data
US 2016/0040124 A1    Feb. 11, 2016

Related U.S. Application Data

(60) Provisional application No. 61/792,613, filed on Mar. 15, 2013, provisional application No. 61/779,845, filed on Mar. 13, 2013.

(51) Int. Cl.
| C12N 5/00 | (2006.01) |
| C12N 5/07 | (2010.01) |
| C07K 14/005 | (2006.01) |
| C12N 7/00 | (2006.01) |
| C12P 21/00 | (2006.01) |

(52) U.S. Cl.
CPC .......... *C12N 5/0601* (2013.01); *C07K 14/005* (2013.01); *C12N 7/00* (2013.01); *C12P 21/00* (2013.01); *C12N 2500/60* (2013.01); *C12N 2511/00* (2013.01); *C12N 2770/36151* (2013.01)

(58) Field of Classification Search
None
See application file for complete search history.

(56) References Cited

U.S. PATENT DOCUMENTS 5,024,947 A    6/1991  Inlow et al.
2013/0344084 A1    12/2013  Subramanian et al.

FOREIGN PATENT DOCUMENTS

WO    WO0166696    9/2001
WO    WO2012130723 A1    10/2012

OTHER PUBLICATIONS

Koval et al., In Vitro Cell. Dev. Biol. (1990) vol. 26, pp. 665-670.*
Kuo et al., Journal of Biomedical Science (2012) vol. 19, pp. 1-12.*
Akahata, Wataru, et al.; "A virus-like particle vaccine for epidemic Chikungunya virus protects nonhuman primates against infection"; Nature Medicine; 2010; 334-339; 16(3).
Akahata, Wataru, et al.; "A Specific Domain of the Chikungunya Virus E2 Protein Regulates Particle Formation in Human Cells: Implications for Alphavirus Vaccine Design"; Journal of Virology; 2012; 8879-8893; 86(16).
Blanchard, P., et al.; "Protection of swine against post-weaning multisystemic wasting syndrome (PMWS) by porcine circovirus type 2 (PCV2) proteins"; Vaccine; 2003; 4565-4576; 21.
Dogan, Ayse Dudu Altinas, et al.; "Tropesygdommen chikungunyafeber er kommet til Europa"; Ugeskr Laeger; 2013; 1716-1719; 175.
Drugmand, Jean-Christophe, et al.; "Insect cells as factories for biomanufacturing"; Biotechnology Advances; 2012; 1140-1157; 30.
Fernandes, Fabiana, et al.; "Insect cells as a production platform of complex virus-like particles"; Expert Rev Vaccines; 2013; 225-236; 12.
Gaige, D.; 'TNMFH Insect Media.xls.' PDF Document, created Mar. 26, 2003. [retrieved on May 27, 2014] Retrieved from Internet: http://ebookbrowsee.net/tnmfh-insect-media-pdf-d298031253.
Gaudin, Yves, et al.; "Mutations in the glycoprotein of viral haemorrhagic septicaemia virus that affect virulence for fish and the pH threshold for membrane fusion"; J. General Virol.; 1999; 1221-1229; 80.
Hacker, David L., et al.; "25 years of recombinant proteins from reactor-grown cells—Where do we go from here"; Biotechnol Adv.; 2009; 1023-1027; 27.

(Continued)

*Primary Examiner* — Jim Ketter
(74) *Attorney, Agent, or Firm* — Henry P. Wu; Gloria M. Fuentes

(57) ABSTRACT

The present invention relates to the use of increased culture pH, relative to standard insect cell culture conditions, during baculovirus infection of lepidopteran insect cells to enable production of recombinant chikungunya (CHIKV) virus like particles (VLPs). The invention further relates to adapted insect cell lines derived from insect cells such as Sf21, which can grow robustly at elevated culture pH, the use of said cell lines to recombinantly produce pH sensitive proteins in the correct conformation and increase expression of recombinant proteins relative to standard insect cell lines. In some embodiments of the invention, the cells are useful for recombinant production of CHIKV VLPs. The invention also relates to a method for the production of a pH-adapted lepidopteran insect cell line. In some embodiments of said method, the cell line is produced and/or maintained in reduced phosphate serum-free insect cell media.

19 Claims, 13 Drawing Sheets

(56) References Cited

OTHER PUBLICATIONS

Hafer, Amanda, et al.; "Differential Incorporation of Cholesterol by Sindbis Virus Grown in Mammalian or Insect Cells"; J. Virol.; 2009; 9113-9121; 83(18).

Ikonomou et al., "Design of an efficient medium for insect cell growth and recombinant protein production", In Vitro Cell. Dev. Biol., 2001, 549-559, 37(9).

Kielian, Margaret, et al.; "pH-Induced Alterations in the Fusogenic Spike Protein of Semliki Forest Virus"; J. Cell Biol.; 1985; 2284-2291; 101.

Koval et al., "pH dependency of cell attachment and growth at both clonal and subculture densities of cultured epidopteran cells"; In Vitro Cell. Dev. Biol., 1990, 665-670, 26(7).

Kuo et al., "Cell-based analysis of Chikungunya virus E1 protein in membrane fusion"; Journal of Biomedical Science, 2012, 1-12, 19(44).

Lee, Chia Yin, et al.; "Chikungunya Virus Neutralization Antigens and Direct Cell-to Cell Transmission are Revealed by Human Antibody-Escape Mutants"; PLoS Pathogens; 2011; e1002390. doi:10.1371/journal.ppat.1002390; 7.

Lee, Regina Ching Hua, et al.; "Mosquito Cellular Factors and Functions in Mediating the Infectious entry of Chikungunya Virus"; PLoS Neglected Tropical Diseases; 2013; 7: e2050EI/E2; 20.

Li, Long; et al.; "Structural changes of envelope proteins during alphavirus fusion"; Nature; 2010; 705-708; 468.

Licari, Peter J., et al.; "Insect Cells Hosts for Baculovirus Expression Vectors Contain Endogenous Exoglycosidase Activity"; Biotechnology Progress; 1993; 146-152; 9.

Liu, Fuxiao, et al.; "Use of baculovirus expression system for generation of virus-like particles; Successes and challenges"; Protein Expression and Purification; 2013; 104-116; 90.

Lu, Yanping E., et al.; "In Vivo Generation and Characterization of a Soluble Form of the Semliki Forest Virus Fusion Protein"; J Virol.; 2001; 8329-8339; 75.

Maiorella, Brian, et al.; "Large-Scale Insect Cell-Culture for Recombinant Protein Production"; Nat Biotech; 1998; 1406-1410; 6.

Medina, Miguel, et al.; "Strong buffering capacity of insect calls: Implications for the baculovirus expresion system"; Cytotechnology; 1995; 21-26; 17.

Metz, Stefan, et al.; "Functional processing and secretion of Chikungunya virus E1 and E2 glycoproteins in insect cells"; Journal of Virology, 2011, 1-12, 8(353).

Metz, Stefan, et al.; "Effective Chikungunya Virus-like Particle Vaccine Produced in Insect Cells"; PLOS Neglected Tropical Diseases, 2013, 1-11(e2124); 7(3).

Moormann, Rob J.M., et al.; "Development of a classical swine fever subunit marker vaccine and companion diagnostic test"; Veterinary Microbiology; 2000; 209-219; 73.

Olejnik, A., et al.; "Effect of hyperosmolarity on recombinant protein productivity in baculovirus expression system"; J. Biotechnol.; 2003; 291-300; 102.

Weiss S. A., et al.; "Insect Cell-Culture Techniques in Serum-Containing Medium"; in Methods in Molecular Biology; Baculovirus Expression Protocols; ed. Richardson, C. D., et al.;1995; 65-202; 39.

Siekavizza-Robles, Carlos, et al.; "Reversible conformational change in herpes simplex virus glycoprotein B with fusion-from-without activity is triggered by mildly acidic pH"; Virology Journal; 2010: 352; 7.

Sourisseau, Marion, et al.; "Characterization of Reemerging Chikungunya Virus"; PLoS Pathog; 2007 e89; 3.

Stanifer, Megan L., et al.; "A Recombinant Vesicular Stomatitis Virus Bearing a Lethal Mutation in the Glycoprotein Gene Uncovers a Second Site Suppressor that Restores Fusion"; J. Virol.; 2011; 8105-8115; 85.

Stiasny, Karin, et al.; "Flavivirus membrane fusion"; J. General Virol.; 2006; 2755-2766; 87.

Sun, Siyang, et al.; "Structural analyses at pseudo atomic resolution of Chikungunya virus and antibodies show mechanisms of neutralization"; ELife; 2013; e00435; 2.

Tramper, J., et al.; "Oxygen gradients in small and big sparged insect-cell bioreactors"; Cytotechnology; 1996; 231-238; 20.

Tramper, J., et al.; "Scale up aspects of sparged insect-cell bioreactors"; Cytotechnology; 1996; 221-229; 20.

Tsetsarkin, Konstantin A., et al.; "A Single Mutation in Chikungunya Virus Affects Vector Specificity and Epidemic Potential"; PLoS Pathog; 2007; e201; 3; 1895-1906.

Van Aarle, P.; "Suitability of an E2 Subunit Vaccine of Classical Swine Fever in combination with the Ems-Marker-Test for Eradication Through Vaccination"; Dev Biol (Basel); 2003; 193-200; 114.

Vashishtha, Malini, et al.; "A Single Point Mutation Controls the Cholesterol Dependence of Semliki Forest Virus Entry and Exit"; The Journal of Cell Biology; 1998; 91-99; 140(1).

Schmid, G.; "Insect Cell Cultivation: Growth and Kinetics" in "Insect Cell Cultures: Fundamental and Applied Aspects"; ed. Vlak, J. M. et al.; Cytotechnology; 1996; 43-56; 20.

Wang, Gongbo, et al.; "Infection of cells by Sindbis virus at low temperature"; Virology; 2007; 461-467; 362.

Weaver, Scott C., et al.; "Chikungunya virus and prospects for a vaccine"; Expert Rev Vaccines; 2012; 1087-1101; 11.

Manon M.J. Cox et al., FluBlok, a next generation influenza vaccine manufactured in insect cells, Biologicals, 2009, 182-189, 37(3).

S.S. Sohi, The effect of pH and osmotic pressure on the growth and survival of three lepidopteran cell lines, in Invertebrate systems in vitro, edited by E. Kurstak et al., Elsevier/North-HollandBiomedical Press, 1980, 35-43.

T.D.C. Grace, Establishment of Four Strains of Cells From Insect Tissues Grown In Vitro, Nature, 1962, 788-789, 195.

\* cited by examiner

SEQUENCE LISTING

```
<160> NUMBER OF SEQ ID NOS: 3

<210> SEQ ID NO 1
<211> LENGTH: 21
<212> TYPE: PRT
<213> ORGANISM: Chikungunya Virus

<400> SEQUENCE: 1

Ala Gln Ile Pro Val His Met Lys Ser Asp Ala Ser Lys Phe Thr His
1               5                   10                  15

Glu Lys Pro Glu Gly
            20

<210> SEQ ID NO 2
<211> LENGTH: 18
<212> TYPE: PRT
<213> ORGANISM: Chikungunya Virus

<400> SEQUENCE: 2

Cys His Pro Pro Lys Asp His Ile Val Asn Tyr Pro Ala Ser His Thr
1               5                   10                  15

Thr Leu

<210> SEQ ID NO 3
<211> LENGTH: 21
<212> TYPE: PRT
<213> ORGANISM: Chikungunya Virus

<400> SEQUENCE: 3
```

```
Cys His Ala Ala Val Thr Asn His Lys Lys Trp Gln Tyr Asn Ser Pro
1               5                   10                  15

Leu Val Pro Arg Asn
            20
```

ADAPTED LEPIDOPTERAN INSECT CELLS FOR THE PRODUCTION OF RECOMBINANT PROTEINS

CROSS-REFERENCE TO RELATED APPLICATIONS

This application is a §371 National Stage Application of PCT/US2014/025277, having an international filing date of Mar. 13, 2014, which claims the benefit of U.S. Provisional Application No. 61/779,845, filed Mar. 13, 2013, and U.S. Provisional Application No. 61/792,613, filed Mar. 15, 2013, the contents of which are herein incorporated by reference in their entirety.

FIELD OF THE INVENTION

The present invention relates to a method for the production of Chikungunya virus (CHIKV) virus-like particles (VLPs) by recombinant expression of CHIKV structural proteins in insect cells, wherein the cells are cultured at an elevated pH, e.g. 6.8 or greater. The invention also relates to a method of producing a pH-tolerant lepidopteran insect cell line that is adapted to grow at elevated culture pH, cell lines produced by said method, and uses of said cell lines to produce pH-sensitive proteins, such as chikungunya virus-like particles.

REFERENCE TO SEQUENCE LISTING SUBMITTED ELECTRONICALLY

The sequence listing of the present application is submitted electronically via EFS-Web as an ASCII formatted sequence listing with a file name "23470USPCT-SEQLIST-11SEP2015.TXT", creation date of Sep. 11, 2015, and a size of 1,398 bytes. This sequence listing submitted via EFS-Web is part of the specification and is herein incorporated by reference in its entirety.

BACKGROUND OF THE INVENTION

Lepidopteran insect cell substrates for recombinant protein production include *Spodoptera frugiperda* IPLB-SF21-AE (Sf21), its more commonly used Sf9 clonal isolate, and various *Trichoplusia ni* cell lines, such as High Five. These cell lines are utilized in the biotechnology industry as host cells in the Baculovirus Expression Vector System (BEVS) for recombinant protein production, or are transfected or transformed with a plasmid DNA expression vector to transiently or stably express a protein of interest (Richardson, C. D. (Ed.), Baculovirus Expression Protocols. *Methods in Molecular Biology* 39:65-202 (1995)).

Sf21 and Sf9 are commonly cultured in commercially available serum-free media formulations which utilize a phosphate buffer system to maintain a culture pH in the optimal range of 6.0-6.4 (Licari et al. Insect cell hosts for baculovirus expression vectors contain endogenous exoglycosidase activity. *Biotechnology Progress* 9: 146-152 (1993) and Drugmand et al. Insect cells as factories for biomanufacturing. *Biotechnology Advances* 30:1140-1157 (2012)) for both cultivation and recombinant protein production. A broader pH requirement of 6.0-6.8 for various insect cell lines has also been previously described, with deleterious effects on cell growth and viability reported upon small deviations outside of this range (Drugmand et al., supra). While the normal culture pH range is suitable for the production of a variety of recombinant proteins, some target proteins cannot be produced effectively in their desired form under these conditions. Viral glycoproteins involved in fusion, often used as vaccine antigens, are one example due to pH-sensitive conformational changes which occur at a threshold pH in the range of typical insect cell culture.

Virions from the *alphavirus* genus contain structural E1 and E2 glycoproteins with a pH threshold for structure conformational change in the range of typical insect cell culture (Lee et al. (2011), supra; Li et al. (2010), supra). Despite this, Sindbis virus has been shown to replicate and produce functional, infectious virions in Sf21 cells when cultured under standard conditions (Hafer et al., Differential incorporation of cholesterol by Sindbis virus grown in mammalian or insect cells. *J. Virol.* 83(18):9113-9121 (2009); and Wang et al. Infection of cells by Sindbis virus at low temperature. *Virology* 362: 461-467 (2007)). Pijlman et al. (WO 2012/130723) report the expression of salmonid *alphavirus* VLPs in insect cells. Chikungunya virus (CHIKV) is a closely related virus for which recombinant virus like particles (VLPs) have been produced in mammalian cell culture (Akahata et al., A virus-like particle vaccine for epidemic Chikungunya virus protects nonhuman primates against infection. *Nature Medicine* 16(3):334-338 (2010)), but when a similar transgene was delivered via baculovirus infection in Sf21, expression of multiple CHIKV proteins was reported without mention of VLP production (Kuo et al. Cell-based analysis of Chikungunya virus E1 protein in membrane fusion. *J. Biomedical Science* 19:44 (2012)).

SUMMARY OF THE INVENTION

The present invention relates to a method for the production of chikungunya virus (CHIKV) virus-like particles (VLPs) comprising: (a) transfecting lepidopteran insect cells with a vector comprising a nucleotide sequence that expresses one or more CHIKV structural proteins; (b) culturing the insect cells in culture medium with a pH from about 6.5 to about 7.8 under conditions that permit expression of the protein and self-assembly of the VLPs; and (c) optionally purifying the VLPs from the culture medium.

Also provided by the present invention is a method for the production of lepidopteran insect cell lines that are capable of growing robustly at an elevated culture pH, e.g. a culture pH that is greater than 6.5, the method comprising use of stress-based adaptation of the insect cells to progressively higher pH.

In one aspect, the invention relates to a method for the generation of an elevated pH-tolerant lepidopteran insect cells comprising: (a) culturing a population of cells from a lepidopteran insect cell line in a standard culture medium that supports the growth of insect cells and has a pH of from about 6.0 to about 6.4; (b) culturing the cells in elevated pH culture medium that has a pH that is greater than the pH of the standard culture medium in step (a); and (c) allowing the cells to adapt to the elevated pH culture medium, wherein the adapted cells exhibit similar growth characteristics to a population of cells of the insect cell line cultured in the standard culture medium. In some embodiments, steps (b) and (c) are repeated one or more times, using an elevated pH culture medium with a pH that is progressively higher each time.

The present invention also relates to high pH-tolerant lepidopteran insect cells which have been adapted to grow in culture media within a pH range of about 6.5 to about 7.8. The pH-tolerant insect cells of the invention can grow robustly at a culture pH typical of mammalian cell culture and higher than that previously recommended for insect cell culture. Said pH-tolerant insect cells are useful for the production of recombinant proteins, including those proteins that require a higher pH than pH 6.4 to maintain correct structural integrity.

Also provided by the present invention are pH-tolerant culture media formulations which are useful for culturing insect cells at an elevated pH. Said media formulations are useful for culturing insect cells at elevated pH and comprise a base medium capable of supporting the growth of insect cells, and about 20 mM or less phosphate, wherein the pH of the pH-tolerant medium is from about 6.8 to about 7.8. In preferred embodiments, the phosphate level of the pH-tolerant culture medium is from about 0.1 mM to about 6.0 mM.

As used throughout the specification and appended claims, the following definitions and abbreviations apply:

The term "elevated pH tolerant," as used interchangeably herein with the terms "pH-tolerant" and "high pH tolerant" refers to an insect cell line or a culture medium, as dictated by the context, which is capable of performing a desired function (e.g. culturing of cells or expression of a recombinant protein) at a pH that is elevated relative to the pH previously recommended for standard insect cell culture, i.e. pH greater than 6.4. In some embodiments of the inventions described herein, the pH is from about 6.8 to about 7.8. In further embodiments, the pH is from about 6.9 to about 7.8, from about 7.0 to about 7.8, from about 7.1 to about 7.8, from about 7.2 to about 7.8, from about 7.3 to about 7.8, from about 6.8 to about 7.6, from about 6.9 to about 7.6, from about 7.0 to about 7.6, from about 7.1 to about 7.6, from about 7.2 to about 7.6, from about 6.8 to about 7.4, from about 6.9 to about 7.4, or from about 7.0 to about 7.4.

Additional abbreviations employed herein include the following: BEVS=baculovirus expression system, CHIKV=chikungunya virus, GFP=green fluorescent protein, TEM=transmission electron microscopy, VLP=virus-like particle, v/v=volume per volume, w/v=weight per volume.

DETAILED DESCRIPTION OF THE INVENTION

Figure 1C:
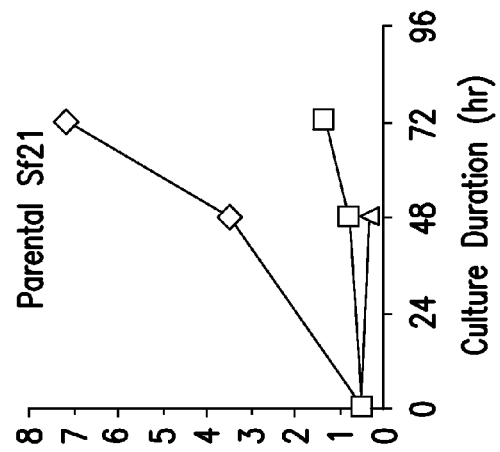
FIG. 1 shows the effect of elevated growth medium pH on cell growth for various *Spodoptera frugiperda* insect cell lines.

Chikungunya virus-like particles (VLPs) have shown potential in multiple animal models for use in a prophylactic vaccine and are currently being evaluated in clinical trials. Scalable, high-level production of these enveloped VLPs by transient gene expression in mammalian cells presents challenges for industrial manufacture. The insect cell baculovirus expression vector system was employed herein as an alternative expression technology. It is shown herein that after standard recombinant baculovirus infection of Sf21 insect cells at pH 6.3, properly processed CHIKV structural proteins were expressed and assembled capsids were observed. However, an increase in culture pH to 6.6-6.8 was necessary to produce detectable concentrations of assembled VLPs. Because such elevated pH exceeds the optimum culture pH for Sf21, a novel insect cell line variant (SfBasic) was derived by exposure of Sf21 to elevated culture pH for a prolonged period of time. The pH adapted SfBasic insect cell line described herein is capable of maintaining normal cell growth into the typical mammalian cell culture pH range of 7.0-7.2, and produces enhanced CHIKV VLP yields relative to the parental Sf21 cell line (see Example 7). After scale-up into stirred tank bioreactors, SfBasic derived VLPs were chromatographically purified and shown to be similar in size and structure to a VLP standard derived from transient gene expression in HEK293 cells. Total serum anti-CHIKV IgG and neutralizing antibody titers from guinea pigs vaccinated with SfBasic-derived VLPs were not significantly different from the corresponding titers of guinea pigs immunized with the VLP standard produced by mammalian cells, suggesting that a pH-adapted insect cell line and production process could be useful for commercial CHIKV VLP manufacturing. It is further shown herein that the adaptation of Sf21 to produce high levels of recombinant protein and VLPs in an elevated pH range is useful for production of other pH-sensitive protein or VLP targets.

Methods for the Production of CHIKV VLPs in Lepidopteran Insect Cells

There is a need for cell substrates and methods for the production of pH-sensitive proteins such as CHIKV VLPs. Due to the low reported culture pH recommended in the art for culturing and propagating lepidopteran insect cells, pH-sensitive proteins which require culture conditions comprising a higher pH (e.g., >6.8), are typically produced in mammalian culture systems.

CHIKV is an arthritic arbovirus (family Togaviridae, genus *Alphavirus*) spread by mosquitoes and capable of causing debilitating, long-term joint pain and arthralgia similar to Dengue. There is currently no CHIKV-specific therapeutic treatment or effective prophylactic vaccine (Weaver et al., Chikungunya virus and prospects for a vaccine. Expert Rev Vaccines 11: 1087-1101 (2012)), and the virus is associated with high rates of morbidity (Sourisseau et al., Characterization of reemerging chikungunya virus. *PLoS Pathog* 3: e89 (2007)). CHIKV outbreaks have occurred in Africa, south Asia, and the Indian Ocean islands, and there is recent evidence of spread to southern Europe (Dogan et al. *Ugeskr Laeger* 175: 1716-1719 (2013)). The recognized insect vector for CHIKV was historically *Aedes egypti*, but a single point mutation in CHIKV has been associated with broadening of the geographical range of disease by increasing virus fitness for the alternative mosquito vector *Aedes albopictus* (Tsetsarkin et al. PLoS Pathog 3: e201 (2007)). This potential for spread of the disease to new areas, including southern Europe and the Americas, has spurred increased research into methods for developing and producing an effective CHIKV vaccine.

CHIKV contains a positive-sense single stranded RNA genome with a 26S sub-genomic sequence that codes for a single structural polyprotein. This structural polyprotein is processed auto-catalytically and by host cell furin and signalase to yield the individual structural proteins that assemble into CHIKV virions (Sourisseau et al., supra). Virions are 60-70 nm in diameter and consist of an icosahedral nucleocapsid composed of 240 copies of capsid protein (C) and a host cell derived envelope containing 240 embedded heterodimers of envelope glycoprotein 1 (E1), and envelope glycoprotein 2 (E2) (Weaver et al., supra, Lee et al. *PLoS Negl Trop Dis* 7: e2050E1/E2 (2013)) heterodimers are presented as trimeric spikes on the surface of mature virions and infected cells, and this E1/E2 complex contains conformational epitopes that give rise to neutralizing antibodies following natural infection or experimental vaccination (Akahata et al., *Nat Med* 16: 334-338 (2010); Akahata et al., *J Virol* 86: 8879-8883 (2012); Sun et al. *ELife* 2: e00435 (2013)). After cell receptor-mediated endocytosis of an infectious CHIKV particle, endosomal acidification drives an irreversible conformational change in E1/E2 that exposes the E1 fusion peptide to mediate fusion with cellular membranes and viral entry into the cytoplasm (Sourisseau et al., supra; Vashishtha et al., *J Cell Biol* 140: 91-99. (1998)). This conformational change can disrupt structural epitopes recognized by neutralizing antibodies, which may be important for the design and production of an effective CHIKV vaccine (Akahata et al. 2012, supra).

Transient transfection of HEK293 cells with a single expression vector carrying the cDNA sequence coding for the CHIKV strain 37997 structural polyprotein is sufficient to produce budded, enveloped CHIKV VLPs that contain an epitope in E1/E2 recognized by the conformation sensitive neutralizing antibody m242 (Akahata et al., 2012, supra, Sun et al., supra). These recombinant CHIKV VLPs are immunogenic in non-human primates (Akahata et al., 2010, supra). Although transient gene expression (TGE) in mammalian cell lines using plasmid DNA expression vectors has advanced significantly in recent years as a recombinant protein production technology, it is still limited by industrial challenges related to increasing recombinant protein yield, manufacturing scale, and lot-to-lot reproducibility (Hacker et al., *Biotechnol Adv* 27: 1023-1027 (2009)). It is shown here that the baculovirus expression vector system (BEVS) is an alternative to TGE for VLP production.

BEVS utilizes an engineered *Autographa californica* multiple nucleopolyhedrovirus (AcMNPV) vector to produce recombinant protein products in lepidopteran insect cell lines. Long used for large-scale recombinant protein production for research use (Maiorella et al. Large-Scale Insect Cell-Culture for Recombinant Protein Production. *Nat Biotech* 6: 1406-1410 (1988)) and veterinary vaccines (Blanchard et al. Protection of swine against post-weaning multisystemic wasting syndrome (PMWS) by porcine circovirus type 2 (PCV2) proteins. *Vaccine* 21: 4565-4575 (2003); van Aarle et al. Suitability of an E2 subunit vaccine of classical swine fever in combination with the E(rns)-marker-test for eradication through vaccination. *Dev Biol* (Basel) 114: 193-200 (2003); Moormann et al. Development of a classical swine fever subunit marker vaccine and companion diagnostic test. *Vet Microbiol* 73: 209-219 (2000)), BEVS has recently emerged as a scalable, candidate production platform for human vaccines. Both enveloped and non-enveloped VLPs have been produced with BEVS, using a single baculovirus vector or co-infection with multiple vectors. Co-expression of multiple subunits from a single baculovirus vector with multiple expression cassettes has also been reported, along with expression of polyproteins which are processed post-translationally into individual mature subunits (Liu et al. Use of baculovirus expression system for generation of virus like particles: Successes and challenges. *Protein Expr Purif* 90: 104-116 (2013); Fernandes et al. Insect cells as a production platform of complex virus-like particles. *Expert Rev Vaccines* 12: 225-236 (2013)).

Recombinant expression of CHIKV E1 and E2 via BEVS has been described previously (Metz et al. Functional processing and secretion of Chikungunya virus E1 and E2 glycoproteins in insect cells. *Virol J* 8: 353 (2011)). Production of CHIKV strain S27 VLPs from Sf21 using a recombinant baculovirus vector was also recently reported (Metz et al. *PLoS Negl Trop Dis* 7: e2124 (2013)).

Previous publications (Wang et al., Infection of cells by Sindbis virus at low temperature. *Virology* 362: 461-67 (2007) and Hafer et al., Differential incorporation of cholesterol by Sindbis virus grown in mammalian or insect cells. *J. Virol.* 83(18): 9113-9121 (2009)) suggest that Sindbis virus, a virus closely related to CHIKV, can replicate and produce infectious virus in Sf21 cells grown under standard culture conditions (pH 6.0-6.3) despite pH-sensitivity of its E1 fusogenic glycoprotein reported in the pH range of Sf21 culture. Kuo et al (Cell-based analysis of chikungunya virus E1 protein in membrane fusion. *J. Biomedical Science* 19:44 (2012)) recombinantly expressed the 26S structural polyprotein of CHIKV by baculovirus infection of Sf21 cells and increased the pH up to 6.9 to demonstrate cell to cell fusion, but did not report formation of VLPs. Many references report detrimental effects on lepidopteran cell cultures at pH outside the optimum range of 6.0-6.3 (See e.g. Drugmand et al., supra).

It was shown herein that cDNA encoding the CHIKV polyprotein could be expressed in insect cells under normal process conditions using the baculovirus expression system (pH in the 6.0-6.4 range), but no VLPs were formed (see EXAMPLE 2). Despite previous publication of the detrimental effects of high pH on insect cells, it is shown herein that increasing the pH outside of the optimum culture pH range for insect cells increases CHIKV VLP production, counter to growth recommendations for insect cells.

To that end, one aspect of the present invention relates to a method for the recombinant production of CHIKV VLPs in lepidopteran insect cells comprising (a) transfecting lepidopteran insect cells with a vector comprising a nucleotide sequence that expresses one or more CHIKV structural proteins; (b) culturing the insect cells in culture medium with a pH from about 6.5 to about 7.6 under conditions that permit expression of the protein and self-assembly of the VLPs; and (c) optionally purifying the VLPs from the culture medium.

While the normal culture pH range of lepidopteran insect cells (pH 6.0-6.4) is suitable for the production of a variety of recombinant proteins, some target proteins cannot be produced effectively in their desired form under these conditions. Viral glycoproteins involved in fusion, often used as vaccine antigens, are one example due to pH-sensitive conformational changes which occur at a threshold pH in the range of typical insect cell culture. Such proteins which can not be optimally produced under normal process conditions for insect cells, i.e. with a culture pH of greater than 6.4, are referred to as "pH-sensitive proteins" herein.

Many virus families contain such proteins, including togaviridae, rhabdoviridae, herpesviridae, and flaviviridae (Kielian et al. pH-induced alterations in the fusogenic spike protein of Semliki Forest virus. *J. Cell Biol.* 101: 2284-2291 (1985); Lee et al., Chikungunya virus neutralization antigens and direct cell-to-cell transmission are revealed by human antibody-escape mutants. *PLoS Pathogens* 7: e1002390. doi:10.1371/journal.ppat.1002390 (2011); Gaudin et al. Mutations in the glycoprotein of viral haemorrhagic septicaemia virus that affect virulence for fish and the pH threshold for membrane fusion. *J. General Virol.* 80: 1221-1229 (1999); Stanifer et al., A recombinant vesicular stomatitis virus bearing a lethal mutation in the glycoprotein gene uncovers a second site suppressor that restores fusion. *J. Virol.* 85: 8105-8115 (2011); Siekavizza-Robles et al., Reversible conformational change in herpes simplex virus glycoprotein B with fusion-from-without activity is triggered by mildly acidic pH, *Virology J.* 7: 352 (2010); Stiasny et al. Flavivirus membrane fusion, *J. General Virol.* 87:2755-2766 (2006); and Li et al., Structural changes of envelope proteins during *alphavirus* fusion. *Nature* 468: 705-708 (2010)). Insect cells maintain an intracellular pH of approximately 7.0 (Medina et al. Strong buffering capacity of insect cells: Implications for the baculovirus expression system. *Cytotechnology* 17: 21-26 (1995)), but these glycoproteins are often in contact with the extracellular environment because they are typically displayed on the surface of cells or virions or are secreted into the culture medium.

Any vector that is capable of being transfected into insect cells can be used for the methods described herein. One skilled in the art can readily determine an appropriate vector for introduction of a nucleotide sequence encoding a CHIKV structural protein, for example, a plasmid vector or a baculovirus vector. In preferred embodiments of the invention, the vector is a baculovirus vector.

Nucleotide sequences for production of CHIKV VLPs include nucleotide sequences that encode any CHIKV structural protein that, when expressed recombinantly under appropriate conditions, can self-assemble into a virus-like particle. In one embodiment, the nucleotide sequence encodes one or more of the CHIKV Capsid, E3, E2, 6K, or E1 proteins. In one embodiment of the invention, the nucleotide sequence encodes a CHIKV polyprotein comprising CHIKV capsid-E3-E2-6K-E1. In another embodiment, the nucleotide sequence is codon-optimized.

In one embodiment of this aspect of the invention, the lepidopteran cells for the production of CHIKV VLPs are *Spodoptera frugiperda* IPLB-SF21-AE (Sf21), a clonal isolate of Sf21 such as Sf9 or a *Trichoplusia ni* cell line, or a pH-adapted derivative of Sf21, Sf9 or *T. ni*. In preferred embodiments, the cell line is Sf21 or a pH-adapted derivative thereof. A pH-adapted lepidopteran insect cell line derivative of the invention is capable of growing robustly at elevated pH, e.g., pH between about 6.5 and about 7.6 and exhibits growth characteristics that are not significantly different than the growth characteristics of the parental cell line under standard insect cell growth conditions.

In one embodiment of the invention, the culture medium has a pH between 6.5 and about 7.8. In an alternative embodiment, the culture medium has a pH between 6.6 and about 7.6. In a further embodiment, the culture medium has a pH between 6.8 and about 7.6. In yet another embodiment, culture medium has a pH between 7.0 and about 7.6. In another embodiment, the culture medium has a pH between 7.0 and about 7.4. In another embodiment, the culture medium has a pH between 6.8 and about 7.4. In further embodiments, the pH of the culture medium is about 6.5, about 6.6, about 6.7, about 6.8, about 6.9, about 7.0, about 7.1, about 7.2, about 7.3, about 7.4, about 7.5, about 7.6, about 7.7, or about 7.8.

In still further embodiments, the CHIKV VLPs are cultured in pH-tolerant culture medium, said medium having an elevated pH, as described in the above embodiments, and comprising a phosphate level that is below 20 mM. In embodiments of the invention, the phosphate level of the pH-tolerant medium is from about 0.1 mM to about 6.0 mM.

The increasing trend of VLP concentration as a function of culture media pH that was observed suggested further investigation of insect cell growth and recombinant protein production at pH>6.5 as a mechanism for increasing CHIKV VLP and/or other recombinant protein production.

Methods for the Generation of pH-Adapted Lepidopteran Insect Cells

To further increase production of CHIKV VLPs in insect cells and to develop a pH-adapted insect cell derivative that was capable of growing robustly at elevated pH, e.g. between 6.5 and 7.8, a stress-based selection was performed and adaptation of Sf21 cells using pH stress to generate a cell line that is tolerate to higher pH and capable of producing recombinant proteins that are typically produced in mammalian cell culture systems. Such pH-adapted lepitopteran insect cell lines may comprise more robust properties and increased capabilities, including recombinant protein production, as compared to the parental cell line. Without wishing to be bound by theory, generation of cell lines with increased capabilities and advantageous characteristics is achieved through selective growth of more robust cells (higher tolerance to the applied stressor), or due to the accumulated physiological changes that allow adapted cells to thrive in conditions which would be inhospitable to the un-adapted parental line.

In one aspect, the present invention is related to a method for the generation of pH-adapted (i.e. "pH-tolerant") lepidopteran insect cells capable of growing robustly at elevated culture pH (e.g., pH 6.5-7.8), said method comprising growing a population of lepidopteran insect cells in culture medium with a standard pH, i.e. between 6.0 and 6.4, and exposing the cells to pH-stress by progressive medium exchange of the cells into higher pH medium. In one embodiment, the parental cells are cultured and adapted using the process described in Example 4 herein.

In embodiments of this aspect of the invention, the lepitopteran insect cells useful as a parental cell line for development of a pH-adapted derivative cell line are selected from Sf21, Sf9 and T. ni. In preferred embodiments of this aspect of the invention, the parental cell line is Sf21.

The invention also relates to a method for the generation of an elevated pH-tolerant lepidopteran insect cell line comprising: (a) culturing a population of cells from a lepidopteran insect cell line in a standard culture medium that supports the growth of insect cells and has a pH of from about 6.0 to about 6.4; (b) culturing the cells in elevated pH culture medium that has a pH that is greater than the pH of the standard culture medium in step (a); and (c) allowing the cells to adapt to the elevated pH culture medium, wherein the adapted cells exhibit similar growth characteristics to a population of cells of the insect cell line cultured in the standard culture medium.

The elevated-pH tolerant insect cells of the invention are capable of growing robustly at elevated culture pH (e.g., pH 6.5-7.8) and exhibit growth characteristics that are similar to the parental cells grown in the original un-modified growth medium (e.g. the population doubling time of the elevated-pH tolerant insect cells is similar to that of the parental cells grown in a standard culture medium).

In embodiments of this aspect of the invention, steps (b) and (c) above are repeated one or more times, using an elevated pH culture medium with a pH that is progressively higher each time. During the process of adaptation, it may be useful or necessary to passage the cells one or multiple times. One skilled in the art can readily determine an appropriate time to passage the cells. In one embodiment, the cells are passaged when the cell concentration is between 0.1 million and 10 million viable cells/mL.

In one embodiment, the methods described above further comprise the step of establishing a cell bank.

In one embodiment of this aspect of the invention, the pH of the elevated pH culture medium in step (b) is from about 6.5 to about 7.0. In another embodiment, the pH of the elevated pH culture medium in step (b) is from about 6.7 to about 7.0. In another embodiment, the pH of the elevated pH culture medium in step (b) is from about 7.0 to about 7.4. In another embodiment, the pH of the elevated pH culture medium in step (b) is about 6.5, about 6.6, about 6.7, about 6.8, about 6.9, about 7.0, about 7.1, about 7.2, about 7.3, about 7.4 or about 7.5.

In embodiments of this aspect of the invention, the elevated pH culture medium comprises less than 20 mM phosphate. In some embodiments, the elevated pH culture medium comprises from about 0.1 to about 6 mM phosphate.

In embodiments of the invention, the insect cell line of step (a) is selected from an Sf9, Sf 21 and a *Trichoplusia ni* cell line. In one embodiment, the insect cell line of step (a) is Sf21.

Expressing pH-sensitive proteins in insect cells was typically not done due to the low reported pH range of lepidopteran cell culture (approximately 6.0-6.4), so such protein targets were typically expressed in mammalian cell systems instead. Adapting Sf21 cells to thrive at this elevated pH extends the advantages of insect cells and BEVS (high expression levels, suspension and serum-free cell growth and protein expression, capability for protein post-translational modifications, proper protein folding/conformation, lack of human adventitious agents, biosafety of cells and virus, etc.) into pH ranges which would have previously excluded BEVS from use. As shown hereon, generation of a new cell line variant through stress-based selection has also led to a cell line which produces many recombinant proteins (11 tested) at equivalent or improved levels relative to the parental Sf21, thus broadening the utility of the new cell line beyond pH-sensitive applications.

pH-Adapted Cell Line

In another aspect, the invention relates to pH-tolerant lepitopteran insect cell lines produced using the methods described herein. The pH-tolerant insect cells of the invention support the improved production of pH-sensitive proteins (including CHIKV VLPs) using DNA vectors or the Baculovirus Expression Vector System (BEVS), as described in more detail, infra.

In one embodiment of the invention, the pH-adapted insect cell line is the MRK-SfBasic cell line described in the Examples herein or equivalent cell line produced by the methods described herein. The relationship of the MRK-SfBasic cell line to published art is as an extension of potential cell culture and recombinant protein expression conditions for the BEVS. Existing lepidopteran cell lines have been derived which extend the range of cell growth temperatures (27-28° C. to 32°+C.) which can be used with Sf9/21 cells, but similar extensions of the culture pH range have not been published. Extension of the culture pH range for insect cells has demonstrable benefits for expressing some types of proteins in their proper conformation which require a higher culture pH than that previously recommended for insect cells. As shown herein, the CHIKV E1 structural protein (in the form of a VLP) is one example. In addition, the MRK-SfBasic cell line retains the ability to produce a range of recombinant proteins under standard BEVS conditions (i.e. not just at elevated pH), and even outperforms commonly used Sf9, Sf21, or *Trichoplusia ni* insect cell lines for a panel of example proteins.

The invention also relates to a pH-adapted lepidopteran insect cell line, derived from parental cell line Sf21, wherein the cell line possesses the properties of increased average cell diameter, increased DNA content per cell, and increased growth rate in elevated pH culture medium relative to the parental Sf21 cell line. In embodiments of this aspect of the invention, the pH-adapted insect cell line yields increased levels of VLPs and recombinant proteins relative to the parental Sf21 cell line.

In specific embodiments of the invention, the pH-adapted insect cell line yields 5-20 fold improvement in CHIKV VLP production relative to the parental Sf21 cell line. In another embodiment, the pH-adapted insect cell line yields an 8-11-fold increase in CHIKV VLP production relative to the parental cells. In another embodiment, the pH-adapted insect cell line yields 1.5-5 fold improvement of recombinant protein production compared to the parental Sf21 cell line.

In embodiments of the invention, the pH of the culture medium is about 6.6 or higher. In alternative embodiments, the elevated culture medium has a pH of about 6.8 or higher, about 7.0 or higher, about 7.1 or higher, about 7.2 or higher, about 6.8 to about 7.5, about 6.8 to about 7.4, about 7.0 to about 7.5, about 7.0 to about 7.4, or about 7.2 to about 7.4.

In embodiments of the invention, the elevated pH of the culture medium is as set forth in any embodiment herein and the average cell diameter of the pH-adapted cell line is about 2 to about 5 μm larger than the parental Sf21 cell line, in alternative embodiments, the cell diameter is about 2 to about 4 μm, about 3 to about 4 μm, or about 3 to about 5 μm larger than the parental Sf21 cells.

In further embodiments, elevated pH of the culture medium is as set forth in any embodiment herein, and the pH-adapted insect cell line has an average cell diameter as set forth in any embodiment herein and further has an approximate 2-fold increase in DNA content per cell. Alternatively, the pH-adapted insect cell line has an about 1.5 to about 3-fold increase in DNA content per cell, about 1.25 to about 2.5-fold increase, or about 1.5 to about 2.5-fold increase relative to parental Sf21.

The invention also provides a pH-adapted lepidopteran insect cell line, derived from parental cell line Sf21, wherein the cell line possesses the properties of about 2 to about 5 μm increased average cell diameter, about 1.5 to about 3-fold increase in DNA content per cell, an increased growth rate in pH culture medium of about 6.8 to about 7.4, and increased CHIKV VLP and/or recombinant protein production relative to the parental Sf21 cell line.

In one embodiment, the pH-adapted insect cell line possesses the properties of about 3 to about 4 μm increased average cell diameter, about 2-fold increase in DNA content per cell, an increased growth rate in pH culture medium of about 7.0 to about 7.4, and increased CHIKV VLP and/or recombinant protein production relative to the parental Sf21 cell line.

In an embodiment of the invention, the lepidopteran insect cell line is the cell line identified herein as SfBasic (alternatively MRK-SfBasic, SfBasic, or MRK-SfBasic), or an equivalent cell line produced by the methods described herein.

Culture Medium

In yet another aspect, the invention provides a culture medium that is formulated for the cultivation of insect cells and the optimal expression of pH sensitive proteins at elevated culture pH. *Spodoptera* cell lines capable of growing robustly under high culture pH conditions (e.g. greater than 6.8) have not been reported in the literature, in part due to limitations of common published insect cell growth media and commercially available serum-free media. These media do not operate well at elevated pH due in part to the use of phosphate species as the primary buffering agent. Increasing the pH of these high-phosphate media causes significant precipitation of media components, which detrimentally impacts cell growth and complicates the adaptation to higher pH. To address this issue, the phosphate concentration of a standard medium was reduced and minimal salt solution and alternative organic buffers were added to allow re-formulation of growth medium at pH≥6.8 and facilitate adaptation and continuous maintenance of high pH-adapted cell lines.

To this end, the invention relates to a pH-tolerant medium for culturing insect cells at elevated pH comprising a base medium capable of supporting the growth of insect cells, and about 20 mM or less phosphate, wherein the pH of the pH-tolerant medium is from about 6.8 to about 7.8. In this aspect of the invention, the pH-tolerant medium may comprise a minimum level of phosphate required for metabolic activity, i.e. a basal level, up to about 20 mM phosphate. The pH-tolerant medium of the invention is useful for culturing insect cells at a pH typical of mammalian cell culture, which allows the use of insect cells as an expression platform for expressing pH-sensitive proteins, which require expression at a higher pH.

In embodiments of the invention, the pH-tolerant medium comprises a phosphate level from about 0.1 to about 20 mM. In preferred embodiments of this aspect of the invention, the medium comprises from about 0.10 to about 6.0 mM phosphate. In another embodiment, the medium comprises from about 0.5 to about 6.0 mM phosphate. In a further embodiment, the medium comprises from about 1.0 to about 6.0 mM phosphate. In still another embodiment, the ph-tolerant medium comprises about 20 mM or less phosphate, about 18 mM or less phosphate, about 16 mM or less phosphate, about 14 mM or less phosphate, about 12 mM or less phosphate, about 10 mM or less phosphate, about 8 mM or less phosphate, about 7 mM or less phosphate, about 6.0 mM or less phosphate, about 5.5 mM or less phosphate, about 5 mM or less phosphate, about 4.5 mM or less phosphate, about 4 mM or less phosphate, about 3.5 mM or less phosphate, about 3.0 mM or less phosphate, about 2.5 mM or less phosphate, about 2.0 mM or less phosphate, about 1.5 mM or less phosphate, about 1.25 mM or less phosphate, about 1.0 mM or less phosphate or about 0.75 mM or less phosphate.

In accordance with the invention, one skilled in the art can determine a specific desired phosphate level appropriate for the pH-tolerant medium for use with a desired application, e.g. expression of a particular recombinant protein. One skilled in the art can readily modify the components of the base medium in order to achieve the desired phosphate concentration, while maintaining desired concentrations of other essential medium components. Base media for use in this aspect of the invention may comprise greater than 20 mM phosphate, which concentration may be reduced, for example by dilution with water or other liquid. Base medium comprising less than the desired amount of phosphate or base medium that is free of phosphate may also be used as a basis for the pH-tolerant medium of the invention. In such case, the phosphate concentration may be increased as necessary with the addition of phosphate, e.g. by addition of sodium phosphate or any other compound that can supply phosphate to the medium, while meeting other desired characteristics of the final medium (e.g. non-toxic).

In preferred embodiments of the invention, the osmolality of the pH-tolerant medium is from about 300 to about 500 mOsm/kg. In one embodiment, the osmolality of the pH-tolerant medium is from about 330 to about 375 mOsm/kg.

In preferred embodiments of this aspect of the invention, the base medium is serum-free, although base media containing serum, such as Grace's media, IPL-41 and TC-100 may also be used.

For the culture medium of the invention herein, the base medium can be any medium that is useful for cultivating/propagating insect cells. Media useful for the cultivation and propagation of insect cells that can be used as a base medium in the present invention are well known in the art. In one embodiment, the base medium comprises a commercially available medium such as Gibco Sf-900 II SFM, BD BaculoGold Max-XP, or Expression Systems ESF921. In further embodiments, the base medium can be, but is not limited to: IPL-41 and derivatives (Sigma-Aldrich, and various other manufacturers), TNM-FH and derivatives (Sigma-Aldrich, and various other manufacturers), Grace's Insect Medium and derivatives (various manufacturers), TC-100 and derivatives (Sigma-Aldrich, and various other manufacturers), Clontech BacPAK Medium, EMD TriEx Insect Cell Medium, EMD BacVector Medium, Expression Systems ESF-AF, Gibco Sf-900 III SFM, Gibco Express Five SFM, Hyclone SFX-Insect, Hyclone SFM4Insect, Hyclone CCM3, Irvine Scientific IS-BAC, Lonza Insect-XPRESS, SAFC EX-CELL TiterHigh, SAFC EX-CELL 420, SAFC EX-CELL 405, SAFC Serum Free Insect Medium-1. The base medium may also be formulated by one of skill in the art following known procedures and discussions of formulation of media for the culturing od insect cells, e.g. U.S. Pat. No. 5,024,947.

Other components may be modified or added to the pH-tolerant culture medium as desired in order to formulate a medium with desired characteristics, e.g. non-toxic, osmolality within a desired range, pH within a desired range, and salt and nutrient components within a desired range. For example, it may be advantageous to add a minimal insect salt solution to provide salt and nutrients to the medium.

The pH-tolerant culture media of the invention are useful for culturing insect cells at a pH typical of mammalian cell culture and may also be useful for the methods described herein, e.g. a method of developing a pH-tolerant insect cell line by progressive adaptation to higher medium pH. As exemplified herein, commercially available serum-free Sf900-II media (Gibco/Invitrogen) was used as a base media for re-formulation at 50% concentration. This media (50% Sf900-II, 50% Merck minimal insect salt solution and organic buffer) was used to adapt the cell line initially, as described in Example 6. After adaptation, 2 similar commercially available media (from BD Biosciences and Expression Systems) were shown to also support similar growth of the newly-adapted cells when re-formulated using the same recipe.

In one embodiment of the invention, the culture medium comprises a base medium, a minimal insect salt solution (MISS) and from about 0.1 to about 20 mM phosphate. In another embodiment, the culture medium comprises a base medium, a minimum insect salt solution (MISS) and from about 0.1 to about 6 mM phosphate. In one embodiment of the invention, the MISS comprises one or more of the following components: sodium, potassium, magnesium, calcium, a carbon source, a non-ionic osmolality adjustment compound, a sheer protectant, which protects against agitation and aeration, and a buffer. Said components may be added to the culture medium through the addition of any compound that provides the desired component and is non-toxic. For example, sodium may be added to the culture medium through the addition of sodium chloride or sodium citrate if sufficient sodium concentration is not already provided by addition of the base medium. The specific counter-ion of the compound selected to provide sodium can be any counter-ion that is not detrimental to the ability of the medium to support cell growth (e.g. does not slow cell growth and is non-toxic). In some embodiments of the invention, the MISS comprises from about 5 mM to about 200 mM sodium chloride.

A non-ionic osmolality adjustment compound can be any compound that is added to the culture medium to modify the osmolality to within a desired range, e.g. between 330 and 375 mOsm/kg. Additionally, a non-ionic osmolality-adjusting compound may be added as needed so that the MISS is isomolar to the base growth medium, i.e. same or no significant differences between the osmolality of the base growth medium and the MISS to prevent the deleterious effects of significant osmolality variation on the cells. Compounds useful in this regard include sugars such as sucrose, glucose, trehalose, xylose, and galactose, non-carbohydrates, salts and other ionic species, as long as such compound is not included in an amount that is detrimental to the cells, e.g. inhibits or slows cell growth or is toxic. In one embodiment of the invention, the pH-tolerant medium comprises MISS that comprises from about 5 mM to about 400 mM sucrose. In another embodiment, the MISS comprises from about 5 mM to about 200 mM sucrose.

In one embodiment of the invention, the MISS comprises a carbon source. Such carbon source may be any compound that is compatible with the desired characteristics of the medium and is not detrimental to the cells. For example, carbon may be provided by the addition of glucose or addition of a carbohydrate that is known to be or discovered to be consumed by insect cells, e.g. fructose or maltose.

In additional embodiments of the invention, the MISS comprises a sheer protectant compound. In some embodiments, the sheer protectant compound is selected from the group consisting of Pluronic F–68 (0.1 to 2.0% w/v), modified celluloses, polyethylene glycols, and polyvinyl alcohols.

Additional buffer can also optionally be included in the pH-tolerant growth medium. Any biological buffer can be added to the pH-tolerant culture media of the invention, as long as said buffer is provided in an amount that is not detrimental to the cells, e.g. an amount that is not so high as to dilute other components of the media so that their concentration is below desired levels. One skilled in the art can readily determine an appropriate buffer that is compatible with insect cells and able to buffer adequately in the desired pH range of 6.8 to 7.8. Useful buffers include, but are not limited to: BES, Bis-Tris, HEPES, Tris, MOPS, TES, Tricine, Glycyl-glycine (Gly-Gly), ACES, Acetate species, Acetic Acid, ADA, BES, Bicarbonate species, Bicine, Bis-Tris, Borate species, Boric Acid, CAPS, CAPSO, CHES, Citrate species, Citric Acid, DIPSO, EPPS, Ethanolamine, Glycyl glycine (Gly-Gly), HEPBS, HEPES, MES, MOBS, MOPS, MOPSO, PIPES, POPSO, Potassium Citrate, Sodium Acetate, Sodium Bicarbonate, Sodium Citrate, TABS, TAPS, TAPSO, TES, Tris base, Tris-HCl, Tricine. Also useful for this aspect of the invention are the Good's series of buffers (see Good et al. Hydrogen ion buffers for biological research. *Biochemistry* 5(2): 467-77 (1966)).

In some embodiments of the invention, a buffer is added to the MISS, which is added to the base medium to reach the desired concentration of each of the essential components. In one embodiment of the invention, MISS is formulated with the non-phosphate organic buffer, N,N-Bis(2-hydroxyethyl)-2-aminoethanesulfonic acid (BES). In another embodiment, the pH-tolerant growth medium comprises a buffer selected from the group consisting of BES, Bis-Tris, HEPES, Tris, MOPS, TES, Tricine, and Glycyl-glycine (Gly-Gly).

In one embodiment of the invention, the MISS comprises one or more components selected from the group consisting of: sucrose, NaCl, KCl, $CaCl_2.2H_2O$, $MgSO_4.2H_2O$, glucose, Pluronic F-68 and BES. In another embodiment of the invention, the MISS comprises one or more components selected from the group consisting of: from about 5 mM to about 400 mM sucrose, from about 5 mM to about 200 mM NaCl, from about 5 mM to about 150 mM KCl, from about 5 to about 50 mM $CaCl_2.2H_2O$, from about 5 to about 50 mM $MgSO_4.2H_2O$, from about 5 mM to about 100 mM glucose, up to about 2% w/v Pluronic F-68 and from about 5 mM to about 200 mM BES. In yet another embodiment, the MISS comprises from about 5 mM to about 400 mM sucrose, from about 5 mM to about 200 mM NaCl, from about 5 mM to about 150 mM KCl, from about 5 to about 50 mM CaCl$_2$.2H$_2$O, from about 5 to about 50 mM MgSO$_4$.2H$_2$O, from about 5 mM to about 100 mM glucose, up to about 2% w/v Pluronic F-68 and from about 5 mM to about 200 mM BES.

In still another embodiment, the MISS comprises one or more components selected from the group consisting of: from about 5 mM to about 200 mM sucrose, from about 5 mM to about 100 mM NaCl, from about 5 mM to about 75 mM KCl, from about 5 to about 25 mM CaCl$_2$.2H$_2$O, from about 5 to about 25 mM MgSO$_4$.2H$_2$O, from about 5 mM to about 50 mM glucose, up to about 1% w/v Pluronic F-68 and from about 5 mM to about 75 mM BES.

In another embodiment, the MISS comprises the following components: from about 5 mM to about 200 mM sucrose, from about 5 mM to about 100 mM NaCl, from about 5 mM to about 75 mM KCl, from about 5 to about 25 mM CaCl$_2$.2H$_2$O, from about 5 to about 25 mM MgSO$_4$.2H$_2$O, from about 5 mM to about 50 mM glucose, up to about 1% w/v Pluronic F-68 and from about 5 mM to about 75 mM BES. Additional component may also be included.

Uses of the pH-Adapted Insect Cell Lines

In one aspect of the invention, pH-tolerant insect cells produced by the methods described herein are used in methods for the production of pH-sensitive proteins. To that end, the invention is related to a method for the recombinant production of a pH-sensitive protein comprising (a) transfecting pH-tolerant lepidopteran insect cells with a vector comprising a nucleotide sequence that expresses a protein that is pH-sensitive; (b) culturing the pH-tolerant insect cells in culture medium with a pH from about 6.5 to about 7.8 under conditions that permit expression of the protein; and (c) optionally purifying the recombinant protein from the cell culture.

In one embodiment of this aspect of the invention, the vector is a baculovirus vector.

In embodiments of the invention, the pH of the culture medium of step (b) above is between 6.6 and about 7.6. In a further embodiment, the culture medium has a pH between 6.8 and about 7.6. In yet another embodiment, culture medium has a pH between 7.0 and about 7.6. In another embodiment, the culture medium has a pH between 7.0 and about 7.4. In another embodiment, the culture medium has a pH between 6.8 and about 7.4. In further embodiments, the pH of the culture medium is about 6.5, about 6.6, about 6.7, about 6.8, about 6.9, about 7.0, about 7.1, about 7.2, about 7.3, about 7.4, about 7.5, about 7.6, about 7.7, or about 7.8.

In one embodiment, the culture medium is a pH-tolerant culture medium of the invention described in any embodiment of any aspect of the invention herein.

In embodiments of this aspect of the invention, the pH-sensitive protein is from a virus family selected from the group consisting of: togaviridae, rhabdoviridae, herpesviridae, and flaviviridae.

As exemplified herein, in order to expand the range of culture conditions available for recombinant protein production in *Spodoptera frugiperda* cells, Sf21 was adapted to grow robustly at an elevated culture pH range (6.8-7.4) relative to previous reports. This slightly alkaline (basic) pH range is more similar to that of typical mammalian cell culture, and thus cultures of the newly derived cell line (henceforth referred to as MRK-SfBasic) are useful to support the recombinant production of more pH-sensitive targets than existing lepidopteran insect cell lines.

Baculovirus-mediated production of pH-sensitive proteins is a significant advantage of the MRK-SfBasic cell line. The Chikungunya virus (CHIKV) is one of several disease-causing members of the *alphavirus* genus (togaviridae family) that contain pH-sensitive, fusogenic envelope glycoproteins on the virion surface.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

EXAMPLE 1

Materials and Methods

Insect Cell Lines and Recombinant Baculovirus Stocks

Recombinant baculovirus stocks for the studies described herein were produced using standard molecular biology procedures well known in the art of baculovirus and insect cell expression; e.g. Bac-to-Bac site-specific transposition in *E. coli* or homologous recombination and plaque purification in insect cells. Lepidopteran insect cell lines (e.g. Sf9, Sf21, or *T. ni*) were maintained in continuous culture according to procedures well known in the art of insect cell culture. See Murhammer, D. W. (Ed.) 2007, Baculovirus and Insect Cell Expression Protocols, 2$^{nd}$ Edition. and Vlak, J. M. (Ed.) 1996, Insect Cell Cultures: Fundamental and Applied Aspects. Specifically, *Spodoptera frugiperda* cell lines Sf21 (Kempbio) and Sf9 (Invitrogen) were cultivated in suspension in serum-free Sf-900II (Gibco) growth media. Cells were maintained and expanded in vented Erlenmeyer shake flasks (Corning) at 27° C. in a shaking incubator (Kuhner) set to 80 RPM and a 2" shaking diameter.

A cDNA fragment coding for the CHIKV strain 37997 structural polyprotein (Genbank accession #AY726732.1) was synthesized (DNA2.0) with flanking 5' EcoRI and 3' XbaI sites, and was then restriction cloned into pFastBac1 (Invitrogen) to produce pFastBac-CHIKV37997. Recombinant baculovirus DNA was generated by Tn7 transposition in DH10Bac *E. coli* using the Bac-to-Bac system (Invitrogen), and the resulting bacmid was transfected into Sf9 cells using Cellfectin-II (Invitrogen) to produce infectious recombinant baculovirus AcMNPV-CHIKV37997. Baculovirus infectious titers were determined using a Guava EasyCyte8HT flow cytometer (Millipore) and a gp64 immunofluorescence Baculovirus Titer Kit (Expression Systems LLC) Immunofluorescence results were converted to plaque forming units (pfu) using the baculovirus standard and analysis template supplied with the Baculovirus Titer Kit. GFP-expessing baculovirus (AcMNPV-GFP, AB Vector) or empty vector baculovirus (AcMNPV-NC, AB Vector) were utilized as negative controls for immunofluorescence and protein analysis methods. Cell counts and cell diameters were determined using a Vi-CELL XR and accompanying image analysis software (Beckman Coulter) using the preloaded Sf21 image analysis algorithm. Population doubling time (PDT) was calculated using time course Vi-CELL XR counts of cultures during exponential growth and standard cellular growth curve fit equations. Statistical analysis of Vi-CELL XR results was performed using Minitab 16 software (Minitab).

Mammalian Cell Line and Expression Vector

HEK293 cells (293-F, Invitrogen) were cultivated and transfected in suspension in serum-free FreeStyle 293 medium (Gibco). Cells were maintained and expanded in vented Erlenmeyer shake flasks (Corning) at 37° C. and 8% $CO_2$ in a shaking incubator (Kuhner) set to 125 RPM and a 2" shaking diameter. A mammalian expression vector was constructed by restriction sub-cloning the same EcoRI/XbaI fragment containing the structural polyprotein sequence from pFastBac-CHIKV37997 into a pV1JNS-based (Youil et al. Comparative analysis of the effects of packaging signal, transgene orientation, promoters, polyadenylation signals, and E3 region on growth properties of first-generation adenoviruses. *Hum Gene Ther* 14: 1017-1034 (2003)) plasmid under control of the hCMV promoter to create pV1JNS-CHIKV37997. This expression vector was transfected into HEK293 cells using 293fectin (Invitrogen) and the manufacturer-supplied protocol to produce positive control cells and culture supernatants containing CHIKV structural proteins and VLPs, respectively. Mock transfections with the CHIKV37997 cassette omitted were utilized as negative controls for immunofluorescence and protein analysis methods. Cell counts and cell diameters were determined using a Vi-CELL XR and accompanying image analysis software (Beckman Coulter) using the pre-loaded HEK293 image analysis algorithm.

Baculovirus Infection of Sf21 in pH-Modified Sf-900II

Serum-free Sf-900II medium (Gibco) at pH 6.3 was adjusted to pH 6.0 using 1N HCl (Sigma-Aldrich) and adjusted to pH 6.6 and 6.8 using 1N NaOH (Sigma-Aldrich). Growth medium pH was measured using a calibrated benchtop pH meter and probe (Fisher Scientific Accumet), and the pH-adjusted medium was sterile filtered through a 0.2 μm Durapore membrane (EMD Millipore). Sf21 cells were centrifuged at 200×g, routine maintenance Sf-90011 media was fully aspirated, and the cells were re-suspended in pH 6.0-6.8 formulations of Sf-900II. Re-suspended Sf21 cultures at 3×106 viable cells/mL were inoculated with AcMNPV-CHIKV37997 in Sf-900II media at an MOI of 1 pfu per cell. 150 mL cultures were inoculated in 500-mL vented Erlenmeyer shake flasks (Corning). Inoculated cultures were incubated at 27° C. in a shaking incubator (Kuhner) set to 80 RPM and a 2" shaking diameter. Cell suspension samples were removed 72 hours post-infection for immunofluorescence flow cytometry. Harvest samples were removed 96 hours post-infection, centrifuged to remove cells, and submitted to qELISA analysis. Statistical analysis was performed using Minitab 16 software (Minitab).

CHIKV VLP Production in Shake Flasks (SF) at Elevated pH

Serum-free Sf21 and SfBasic cultures at 3×106 viable cells/mL were inoculated with AcMNPV185 CHIKV37997 in Sf-900II media at an MOI of 0.1 pfu per cell. 35 mL cultures were inoculated in 125-mL vented Erlenmeyer shake flasks (Corning), and 300 mL cultures were inoculated in 2-L vented Erlenmeyer shake flasks (Corning). Inoculated cultures were incubated for 24 hours at 27° C. in a shaking incubator (Kuhner) set to 80 RPM and a 2" shaking diameter to initiate the infection. Infected cells were centrifuged at 200×g, the Sf-900II media was fully aspirated, and cells were re-suspended in pH 7.4 Sf-900II-BES-MISS for VLP production. Culture pH was maintained between 7.0-7.4 by monitoring the pH of samples via calibrated benchtop pH meter and probe (Fisher Scientific Accumet) and aseptically adding sterile 1 N NaOH at a rate of 15 μL of 1 N NaOH/pH unit/mL of culture. Samples were removed at 72 and 96 hours post-infection, centrifuged to remove cells, and submitted to qELISA analysis. Data points without explicit time-point indications are 96 hour post-infection harvest samples. Statistical analysis was performed using Minitab 16 software (Minitab).

CHIKV VLP Production in Stirred Tank Bioreactors (STBR) at Elevated pH

Serum-free SfBasic cultures at 3×106 viable cells/mL were inoculated with AcMNPV-CHIKV37997 in Sf-900II media (Gibco) at an MOI of 0.1 pfu per cell. 2 L cultures were inoculated in 3-L jacketed glass bioreactors (Sartorius) and controlled using a BioStat MD2 bioreactor control system (Sartorius). The culture was agitated with two 5.8 cm diameter pitched blade, low-shear impellers (Sartorius) at a constant 100 RPM, and temperature was maintained at 27° C. using a PID loop to control the jacket water temperature. Aeration and gas exchange were accomplished using a ring sparger supplying 50 sccm of air and an overlay port supplying 200 sccm of air. Dissolved oxygen was controlled at 40% saturation (relative to culture media at equilibrium with ambient air) by a PID-controlled gas flow controller delivering pure oxygen at 40-100 sccm via the ring sparger. 24 hours after inoculation, the culture was centrifuged at 200×g and Sf-900II media was fully exchanged for pH 7.4 Sf-900II-BES-MISS media to promote VLP production. Culture pH was subsequently controlled at 7.2 by a PID-controlled peristaltic pump delivering sterile 1 N NaOH (Sigma-Aldrich) as required by the process. Samples were removed at 48, 72, and 96 hours post-infection, centrifuged to remove cells, and submitted to qELISA analysis.

Antibodies

Peptides corresponding to regions of CHIKV capsid, E1, and E2 proteins were synthesized and conjugated to Keyhole limpet hemocyanin (KLH, Covance). Anti-capsid antibody Ab3840 was raised against peptide AQIPVHMKSDASK-FTHEKPEG (SEQ ID NO:1), anti-E1 antibody Ab3845 was raised against peptide CHPPKDHIVNYPASHTTL (SEQ ID NO:2), and anti-E2 antibody Ab3850 was raised against peptide CHAAVTNHKKWQYNSPLVPRN (SEQ ID NO:3). All peptide-KLH conjugates were emulsified in Freund's Complete Adjuvant (FCA, Covance) for initial injections and emulsified in Freund's Incomplete Adjuvant (FIA, Covance) for all subsequent booster injections. Animals were injected subcutaneously (SC) with a 500 microgram peptide initial dose in FCA at Day 0, and subsequently injected SC with 500 microgram peptide doses in FIA at Day 21, 42, and 63. Intermediate bleeds containing approximately 20 mL of serum were removed at Day 52 and Day 73, and a final bleed containing approximately 50 mL of serum was removed at Day 77. Antibodies were isolated from serum samples using Protein G Sepharose Fast Flow resin (GE Healthcare) and eluted into a pH 7.4 phosphate buffered saline (PBS) solution. Hybridoma cell lines producing monoclonal antibodies m242 and m10-18 (Akahata et al. 2012, supra, Sun et al., 2013, supra) were supplied by the NIH Vaccine Research Center through a Cooperative Research and Development Agreement (CRADA). After standard hybridoma culture, antibodies were harvested from the cell culture supernatant using Protein G Sepharose Fast Flow resin (GE Healthcare) and eluted into a pH 7.4 phosphate buffered saline (PBS) solution.

CHIKV VLP Standard

A purified CHIKV strain 37997 VLP preparation was obtained for use as a VLP standard from the NIH Vaccine Research Center (VRC) through a CRADA. Briefly, VLPs were produced by HEK293 cells using polyethylenimine (Polysciences) mediated transient transfection of a plasmid DNA construct described previously (Akahata et al., 2010, supra). HEK293 cells were transfected in FreeStyle 293 (Gibco) after adaptation to suspension, serum-free growth in EX-CELL 293 medium (SAFC). The cell culture supernatant was harvested via centrifugation and then clarified using a 0.45 mm PVDF filter (EMD Millipore). The clarified supernatant was concentrated 5-fold and diafiltered into a sucrose phosphate buffer (11 mM phosphate, 7.2% w/v Sucrose, pH 7.0) and then loaded to a Q Sepharose XL anion-exchange column (GE Healthcare). While bound to the resin, the VLPs were washed with the phosphate buffer and phosphate buffer supplemented with Benzonase endonuclease (EMD Millipore). VLPs were eluted with a citrate phosphate buffer (11 mM phosphate, 25 mM citrate, 7.2% w/v sucrose, pH 7.2) and diafiltered against citrate phosphate buffer (11 mM phosphate, 25 mM citrate, 7.2% w/v sucrose, pH 7.2). The VLPs were then filter-sterilized using 0.22 mm PVDF filters (EMD Millipore) and stored at −70° C. until further use.

SDS-PAGE and Western Blot

Sf21 cell lysates and culture supernatant samples were denatured for SDS-PAGE separation by mixing with Tris-Glycine reducing sample buffer (Invitrogen) containing SDS and DTT and heating for 10 minutes at 75° C. Denatured samples were loaded into a 4-20% Tris-Glycine pre-cast gel (Invitrogen) with MagicMark XP and Novex Sharp Pre-stained molecular weight markers (Invitrogen). Equivalent cell culture volumes or density gradient ultracentrifugation fraction volumes were loaded in each well to facilitate qualitative image-based comparisons. After electrophoresis, proteins were transferred to a nitrocellulose membrane using the iBlot transfer device and stack (Invitrogen). Membranes were blocked for 2 hours at room temperature using 5% nonfat dry milk (Bio-Rad) in Tris-buffered saline with Tween-20 (TBST, Santa Cruz Biotech), and then washed 3×5 minutes in TBST. Washed membranes were incubated with primary antibodies diluted in TBST for 2 hours at room temperature. Anti-capsid Ab3840, anti-E1 Ab3845, and anti-E2 Ab3850 were used at a 1:430 dilution, and anti-Chikungunya 181/25 pAb (IBT Bioservices) was used at a 1:1000 dilution. Membranes were washed 3×5 minutes in TBST and then treated for 2 hours with goat anti-rabbit IgG monoclonal antibody-alkaline phosphatase (AP) conjugate (Santa Cruz Biotech), diluted 1:2000 in TBST. Membranes were washed 3×5 minutes in TBST, and then developed in NBT/BCIP 1-Step (Thermo-Pierce) for 5 minutes. The reaction was quenched by rinsing with distilled water, and developed blot membranes were scanned using an ImageScanner II imager with accompanying LabScan software (GE Healthcare). Dashed lines indicate different sections of the same gel. SDS-PAGE purity gels for purified VLP preparations were stained with Coomassie Blue, scanned using an ImageScanner II imager with accompanying LabScan software (GE Healthcare).

Immunofluorescence Flow Cytometry

Immunofluorescence surface staining with m242 was utilized as an indicator of the quantity of pre-fusion, conformationally correct E1/E2 complex displayed on the plasma membrane of cells. To prevent internalization of antibodies, all wash, block, and stain solutions were cold (2-8° C.) and samples were kept on ice. AcMNPV-CHIKV37997 and AcMNPV-NC infected Sf21 cells were harvested after 3 days by gentle centrifugation and washed once with pH 7.2 PBS+1% Blocker BSA (Thermo). HEK293 cells transfected with pV1JNS-CHIKV37997 or mock transfected were harvested after 3 days and washed once with pH 7.2 PBS+1% Blocker BSA (Thermo). Washed cells were re-suspended in a preparation of m242 at 7 μg/mL in pH 7.2 PBS (1:250 dilution) and incubated at 2-8° C. for 2 hours. The cells were washed twice with pH 7.2 PBS+1% Blocker BSA, labeled with a goat anti-mouse IgG monoclonal antibody-AlexaFluor 488 conjugate (Molecular Probes), and incubated at 2-8° C. for 2 hours. Labeled cells were washed twice with pH 7.2 PBS+1% Blocker BSA, and then analyzed immediately using a Guava EasyCyte8HT capillary flow cytometer (Millipore). AlexaFluor488 green fluorescence data was produced using GuavaSoft 2.2 software (Millipore), and statistical analysis was performed using Minitab 16 software (Minitab).

Dynamic Light Scattering (DLS)

Purified VLP preparations derived from SfBasic and HEK293 were loaded directly into a 40 μL low volume quartz cuvette (Malvern) and analyzed in triplicate using a ZetaSizer Nano and accompanying software (Malvern Instruments). Standard protein material and water dispersant parameters were applied from the software package, and triplicate analyses were averaged for visualization of the size distribution. Size distribution data was exported to Minitab 16 software (Minitab) for calculation of mean particle diameter and 95% confidence intervals, as well as statistical hypothesis testing.

Cell Cycle and Propidium Iodide Analysis

Un-infected Sf21 and SfBasic cells were fixed and permeabilized for one hour at 2-8° C. in 70% ethanol in PBS (Sigma-Aldrich). A Guava Cell Cycle Kit (Millipore) was used to stain the cells for flow cytometry analysis using a Guava EasyCyte8HT capillary flow cytometer (Millipore) and the manufacturer-supplied cell cycle procedure. Cell cycle data was analyzed using the standard Cell Cycle program from the GuavaSoft 2.2 software package (Millipore). Ethanol-fixed Sf21 and SfBasic cells were also independently stained with propidium iodide (Molecular Probes) and imaged using a propidium iodide filter set and a fixed exposure time and magnification on an IX70 fluorescence microscope (Olympus) with SPOT 4.7 image capture software (SPOT Imaging Solutions).

Density Gradient Ultracentrifugation

Sucrose density gradients spanning a calculated density range from 1.16-1.20 g/mL were constructed in Ultra-Clear centrifuge tubes (Beckman) by standard gradient methods. The sucrose gradient was generated in a 150 mM NaCl, 10 mM Tris, 1 mM EDTA, pH 8.0 buffer solution (Sigma-Aldrich). Culture supernatants from SfBasic or HEK293 VLP production cultures were treated with 0.2 volumes of 5 M NaCl (Sigma-Aldrich) on ice for 10 minutes, and then gently layered on top of the sucrose gradient solution. Loaded gradient tubes were centrifuged at 50,000×g for 4 hours in a SW41Ti rotor (Beckman) controlled at 16° C. throughout centrifugation. Fractions were collected for Western blot analysis.

Animals and Vaccination

Hartley guinea pigs were obtained from Charles River Laboratories. Purified CHIKV VLPs derived from infection of SfBasic with AcMNPV-CHIKV37997 and VLP standard derived from transient transfection of HEK293 cells were adjuvanted onto Adju-Phos aluminum based adjuvant (Brenntag Biosector). Guinea pigs (4 animals per group) were vaccinated intramuscularly with doses of 0.01, 0.10, 1.0, or 10 micrograms of CHIKV VLP as measured by qELISA Animals were vaccinated at Day 0 and Day 14, and blood was sampled on Day 14 (prior to dosing) and on Day 21 (at study completion). A pre-vaccination serum sample was taken prior to the first vaccination for the purpose of setting the serum IgG ELISA background.

VLP Electron Microscopy and Analysis

Electron microscopy was performed at NanoImaging Services (La Jolla, Calif., USA). Purified VLP samples were preserved in vitrified ice supported by holey carbon films on 400-mesh copper grids. Samples were prepared for imaging by applying a 3 µL drop of sample suspension to a cleaned grid, blotting with filter paper, and immediately proceeding with vitrification in liquid ethane. Grids were stored under liquid nitrogen until transfer to the electron microscope for imaging. Electron microscopy was performed using an FEI Tecnai T12 electron microscope, operating at 120 keV equipped with an FEI Eagle 4 k×4 k CCD camera. Vitreous ice grids were transferred into the electron microscope using a cryostage that maintains the grids at a temperature below −170° C. Images of each grid were acquired at multiple scales to assess the overall distribution of the specimen. After identifying potentially suitable target areas, pairs of high magnification images were acquired at nominal magnifications of 52,000× (0.21 nm/pixel) and 21,000× (0.50 nm/pixel). The images were acquired at a nominal underfocus of −4 µm (52,000×) and −5 µm (21,000×) and electron doses of 10-25 e-/Å2.

Individual particles in the 21,000× magnification images were selected using automated picking protocols (Lander et al., *J Struct Biol* 166: 95-102. (2009)). A reference-free alignment strategy based on the XMIPP processing package (Sorzano et al., *J Struct Biol* 148: 194-204 (2004)) was then applied. Algorithms in this package aligned the selected particles and sorted them into self-similar groups of classes. The XMIPP package uses the Kernel Probability Density Estimator Self-Organizing Map (KerDenSOM) classification method (Pascual-Montano et al., *J Struct Biol* 133: 233-245 (2001)), which maps a set of high dimensional input vectors into a regular two-dimensional grid so that the proximity of the units in the map reflects the similarity of the input data. SfBasic-derived particles and HEK293-derived VLP standard particles were counted and evaluated, and 2D class averaged VLP images were produced from 148 and 199 high quality particle images for SfBasic-derived and HEK293-derived VLPs, respectively. Image-based fractional counting of putative CHIKV particles (round, 50-70 µm in diameter) and baculovirus particles (rod-like, 300-400 nm in length) was also performed for a set of images from the SfBasic-derived sample, including 422 total particles.

Thin-Section TEM of Cells

Electron microscopy was performed at NanoImaging Services (La Jolla, Calif., USA). AcMNPV384 CHIKV37997 infected Sf21 cells in pH 6.3 Sf-900II (Gibco) and pV1JNS-CHIKV37997 transfected HEK293 cells were fixed overnight at 4° C. using 2.5% glutaraldehyde in 0.1 M Sodium cacodylate buffer with 1 mM CaCl2, pH 7.3 (NanoImaging Services). Samples were prepared using standard embedding and thin sectioning procedures and a continuous carbon grid method. Grids were nitrocellulose supported 400-mesh and slotted copper. Samples were stained with 2% uranyl acetate for imaging. Electron microscopy was performed using an FEI Tecnai T12 electron microscope, operating at 120 keV equipped with an FEI Eagle 4K×4K CCD camera. Negative stain grids were transferred into the electron microscope using a room temperature stage. Images of each grid were acquired at multiple scales to assess the overall distribution of the specimen. After identifying potentially suitable target areas, pairs of high magnification images were acquired at nominal magnifications of 52,000× (0.21 nm/pixel), 21,000× (0.50 nm/pixel), and 15,000× (0.71 nm/pixel). The images were acquired at a nominal underfocus of −4 μm (52,000×), −5 μm (21,000×) and −10 μm (15,000×) and electron doses of 2-30 e-/Å2. A high magnification tilt series was acquired at a nominal magnification of 21,000× (0.50 nm/pixel), nominal underfocus of −5 μm, and electron doses of 2-4 e-/Å2.

Serum IgG ELISA

Anti-CHIKV IgG titers were determined by immobilizing purified CHIKV VLPs onto a plate and determining the antigen binding endpoint IgG concentration of serum samples using a standard ELISA format in duplicate. Briefly, Maxisorp 96F plates (Nunc) were coated with 0.2 mg/mL of CHIKV VLP standard in PBS overnight and blocked with 1% BSA in PBS with 0.05% Tween 20. 100 μL of serial dilutions of guinea pig serum samples were added to the wells, incubated for 1 hour, and washed. Bound guinea pig IgG was detected using a goat anti-guinea pig IgG horseradish peroxidase conjugate (Jackson Laboratories). Signal was developed from bound peroxidase using the chromogenic substrate 3,3',5,5'-tetramethylbenzidine (Thermo-Pierce) and sulfuric acid to quench. Plates were read at 450 nm using a spectrophotometer (Beckman Coulter), and the serum titer was determined by taking the reciprocal of the highest dilution factor which produced a signal at least 3-fold greater than background signal. Graphs and statistics were generated with the GraphPad Prism 5 software package (GraphPad Software). Geomean antibody titers (N=4 animals per group) are reported graphically with each animal represented by a data point, and the nonparametric Kruskal-Wallis test was applied with Dunn's post-test for pairwise comparisons between dose-matched groups vaccinated with VLPs derived from HEK293 or SfBasic. Indications of background signal represent the geomean titer of pre-vaccination serum samples for all animals.

CHIKV VLP Quantitative ELISA (qELISA)

A quantitative enzyme-linked immunosorbent assay (qELISA) was used to quantify assembled VLPs using neutralizing antibodies directed at spatially overlapping conformational epitopes on E2 when assembled in the E1/E2 complex. Total protein content for the HEK293-derived VLP standard was quantified using a BCA Protein Assay kit (Thermo-Pierce) and the manufacturer-supplied protocol. A BCA standard curve was prepared by independent dilution of 2 mg/mL albumin to 0.5-500 μg/mL. Standards and samples were plated on the plate (25 μL) and mixed with 200 μL of the BCA working reagent. The plate was shaken, incubated at 37±5° C. for 30 minutes, cooled to room temperature (RT), and read by a plate reader. SOFTmaxPRO software (Molecular Devices) was used to analyze the results, and a quadratic fit was used for the standard curve. 384-well microplates were coated at ambient temperature for 60 minutes with m242, an E2-specific neutralizing antibody. After washing and blocking, fifteen 1.67-fold serial dilutions of the VLP standard and test articles were generated, and 75 μL per well of each dilution was plated. After a 60 minute incubation and a plate wash step, 30 μL of 0.5 μg/mL biotinylated m10-18, another E2-specific neutralizing antibody, was added to the plate. The complex was washed, and signal was developed by the addition of streptavidin-alkaline phosphatase conjugate and the fluorogenic substrate, 4-methylumbelliferyl phosphate (4-MUP). A standard curve was generated by plotting fluorescence intensity (excitation 360 nm/emission 465 nm) as a function of the logarithm of analyte concentration. The resulting curve was fit with a four-parameter logistic equation, and unknown sample concentrations were determined by interpolation from the VLP standard curve. The limit of quantitation (LOQ) was determined to be 2 ng/mL relative to the VLP standard, and Sf21, SfBasic, and HEK293 negative control samples were confirmed as less than LOQ.

Serum Neutralization Assay

Guinea pig sera were analyzed in duplicate using a 100% neutralization titration (NT100) with CHIKV strain 181/25 (Levitt et al., Vaccine 4: 157-162. (1986)). One day prior to CHIKV infection, Vero cells (American Type Culture Collection) were plated at 15,000 cells/well in a 96 well plate (Nunc). Neutralization titers were determined by mixing serial dilutions of guinea pig sera with 350 PFU of CHIKV 181/25 and incubating for 1 hour at 37° C. After the incubation, samples were added to Vero cell monolayers and incubated for 3 days. Vero cell monolayers were subsequently fixed and stained with 0.05% crystal violet, 20% methanol (Sigma-Aldrich). Neutralization titers were determined by taking the reciprocal of the last dilution where the Vero cell monolayer remained fully intact. Graphs and statistics were generated with the GraphPad Prism 5 software package (GraphPad Software). Geomean titers (N=4 animals per group) are reported graphically with each animal represented by a data point, and the nonparametric Kruskal-Wallis test was applied with Dunn's post-test for pairwise comparisons between dose-matched groups vaccinated with VLPs derived from HEK293 or SfBasic.

Purification of VLPs

Cell supernatants from culture batches were harvested via centrifugation, pooled and Halt™ protease inhibitor (Pierce Biotechnology, Rockford, Ill.) was added to the supernatant. The batch was clarified using 0.45 µm and 0.2 µm Durapore® filters (EMD Millipore, Billerica, Mass.) and 2 mm EDTA was added. The batch was then concentrated and exchanged to 150 mM NaCl/20 mm HEPES pH 8 buffer using a 500 kDa ultrafiltration filter (GE Healthcare, Westborough, Mass.). The ultrafiltration product was treated with Benzonase® endonuclease (EMD Millipore, Billerica, Mass.) followed by 0.45/0.22 µm Durapore® filtration (EMD Millipore, Billerica, Mass.). The filtrate was loaded to a Sephacryl™ S-400 HR size exclusion column (GE Healthcare, Pittsburgh, Pa.) with 300 mM NaCl/20 mM HEPES pH 8 mobile phase. The eluate was filtered through a 0.2 µm Durapore® filter (EMD Millipore, Billerica, Mass.), then exchanged to 20 mM HEPES pH 8 buffer using Sephadex® G25 columns (GE Healthcare, Pittsburgh, Pa.). The batch was then loaded to a Q Sepharose™ XL anion exchange column (GE Healthcare, Pittsburgh, Pa.) and eluted by NaCl gradient. The eluate was concentrated and exchanged into 11 mM potassium phosphate/25 mM sodium citrate/218 mM sucrose pH 7.2 buffer using a 500 kDa ultrafiltration filter (GE Healthcare, Westborough, Mass.) with final concentration by 30 kDa Amicon® Ultra filters (EMD Millipore, Billerica, Mass.). The ultrafiltration product was filtered through a 0.2 µm Durapore® membrane (EMD Millipore, Billerica, Mass.) and purified VLPs stored at −70° C.

Characterization of Cell Lines

Cell diameters and cell counts were established microscopically using Beckman Vi-CELL XR cell counter and image analysis software. Viable cell counts and cell viabilities were determined using the Vi-CELL XR trypan blue exclusion reagent and sample processing.

Analysis of DNA content was performed using a Millipore Guava easyCyte 8HT flow cytometer and Guava Cell Cycle reagent kit (propidium iodide nucleic acid stain) according to manufacturer's protocol. The resulting DNA staining flow cytometry data was analyzed using Millipore GuavaSoft to determine relative DNA content.

Population doubling time (PDT) was determined using Vi-CELL XR cell count and the standard calculation method: LN(2)/slope of linear fit (natural logarithm of cell count as function of culture time).

EXAMPLE 2

Expression of CHIKV Polyprotein in Insect Cell Lines Using Standard Insect Cell/Baculovirus Expression Process Sf9, Sf21, and $T.\ ni$ cells (supplied by Invitrogen; Life Technologies Corp., Carlsbad, Calif.) were grown in suspension culture in commercially available growth medium (Sf-900™ III serum free medium (SFM) and Express Five® SFM (Life Technologies Corp), pH approximately 6.0-6.4) per manufacturer's recommendations and protocols well known in the art of insect cell culture (see Example 1). These cell cultures were infected with a recombinant baculovirus carrying cDNA coding for the CHIKV structural polyprotein (Capsid-E3-E2-6K-E1, UniProtKB/Swiss-Prot accession AAU43881.1) under control of the AcMNPV polyhedrin promoter to generate AcMNPV-CHIKV37997. Cell density at infection ranged from 1-2 million viable cells/mL with a multiplicity of infection (MOI) of approximately 0.1 pfu/cell. Samples were removed from the baculovirus-infected cell cultures 4 days post-infection and then centrifuged to separate cells from supernatant. The cell pellet and clarified culture supernatant were subjected to Western blot analysis and a sandwich format ELISA. Standard Western blot techniques with a polyclonal anti-CHKV antibody (IBT Biservices, Gaithersburg, Md.) were used to confirm recombinant expression of CHIKV proteins. Sandwich ELISA was performed as described in EXAMPLE 1 to quantitate concentration of VLPs. Supernatant samples were also ultracentrifuged at 50,000×g for 1.5 hours through an iodixanol density gradient to separate out VLPs and concentrate (if present).

Recombinant CHIKV protein bands were observed at the approximate expected molecular weight (E1, E2, and Capsid) by Western blot of cell pellet lysates, but not in culture supernatants. Strain 37997 structural polyprotein was expressed and processed into individual structural proteins intracellularly when Sf21 cells were infected in standard Sf-900II medium with AcMNPV-CHIKV37997. CHIKV E2 was correctly processed at the furin recognition site to cleave E3 from E2, but the presence of a band consistent with p62 (E3/E2) suggests incomplete cleavage. The same p62 band was also detected in the HEK293 cell positive control lysate on the same gel, indicating that incomplete processing by furin in Sf21 cells is unlikely to preclude the production of CHIKV VLPs. CHIKV E1 was produced by infected Sf21 cells and efficiently cleaved from 6K via signalase to produce mature E1. CHIKV capsid protein was also expressed and auto-catalytically cleaved from E3 as expected.

A quantitative ELISA assay (qELISA) was used to quantify the concentration of VLPs using anti-E2 neutralizing antibodies m242 and m10-18, which bind spatially overlapping conformational epitopes presented by the pre-fusion E1/E2 complex. Binding of antibody m242 has been reported to prevent E1/E2 conformational change (Akahata et al., 2012, supra). The binding sites for these antibodies have also been defined in a 5.3 Å resolution cryo-electron microscopy (cryoEM) map of CHIKV VLPs (Sun et al., 2013, supra), confirming their specificity for detection of epitopes presented on VLPs. The limit of quantitation (LOQ) for this sensitive qELISA was determined to be 2 ng/mL, relative to a purified CHIKV VLP standard derived from transient transfection of HEK293 cells.

Despite the presence of processed E1, E2, and capsid protein in Sf21 cell lysates, the corresponding Sf21 culture supernatants produced no detectable signal in the VLP-indicating qELISA assay. However, thin-section TEM images of the cytoplasm of AcMNPV-CHIKV37997 infected Sf21 cells revealed the formation of large clusters of approximately 30-35 nm diameter particles that were less electron dense than baculovirus nucleocapsids. Similar particles and clustered arrays were observed to be prevalent in transfected HEK293 cells that produced budded CHIKV VLPs, but were not observed in surveys of negative control images of Sf21. Putative CHIKV capsids were consistent with previous descriptions of CHIKV capsids (Chen et al., *Virol J* 10: 169 (2013)), suggesting that capsid formation and organization in the cytoplasm was likely not responsible for preventing VLP budding into the supernatant.

A repeat infection performed in cholesterol-supplemented growth media produced similar results to the standard infection process (data not shown), despite the cholesterol dependence for budding of the related SINV and SFV (Lu et al., *J Virol* 73: 4272-4278 (1999); Marquardt et al. *J Cell Biol* 123: 57-65. (1993); Vashishtha et al., *J Cell Biol* 140: 91-99 (1998)). Acylation of E1 and E2 is also involved in *alphavirus* budding, but was not investigated due to the documented ability of insect cells to palmitoylate the glycoproteins of AcMNPV, Marburg virus, and SFV (Zhang et al. *J Virol* 77: 6265-6273 (2003); Funke et al. *Virology* 208: 289-297 (1995); Scharer et al. *Arch Virol* 132: 237-254 (1993)). Taken together, these observations suggested that Sf21 cellular or culture conditions may be influencing the conformation and stability of the E1/E2 complex thought to be involved in budding (Akahata et al., 2012, supra).

This experiment demonstrated that recombinant CHIKV proteins could be produced in the standard insect cell/baculovirus expression system, but VLPs did not properly form (i.e. as in transiently transfected HEK293 culture) under these standard conditions.

EXAMPLE 3

Parental Cell Line Selection

Figure 1B:
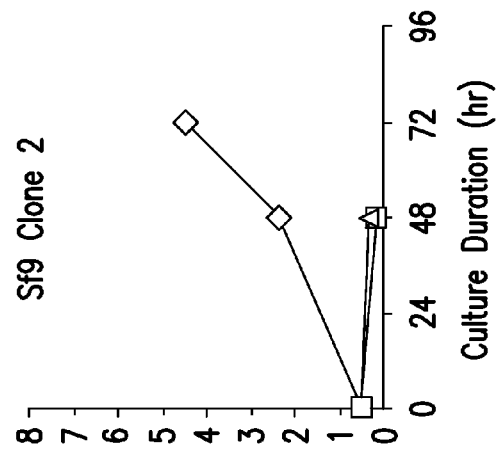
Figure 1A:
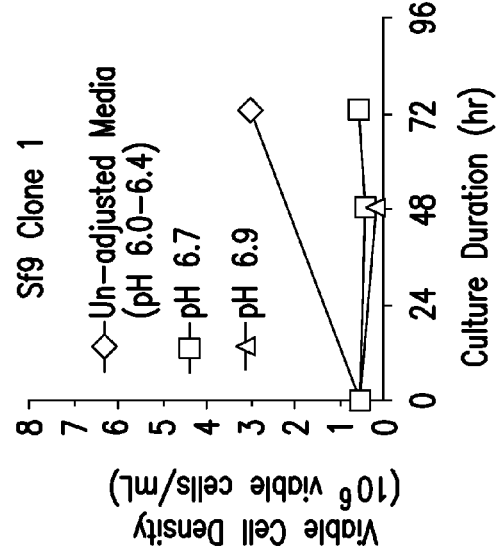

Several insect cell line variants (two Sf9 clones, and Sf21) were subjected to high pH stress to determine their resistance to high pH conditions. Sf-900™ (II or III) SFM was pH adjusted upward to various elevated pH levels by addition of NaOH to sterile growth medium. Each insect cell line variant was sub-cultured directly into the same series of pH-adjusted media formulations, and cell count and cell viability were monitored using Beckman Vi-CELL XR cell counter and image analysis software. Although Sf9 is more commonly used and is reported to be more tolerant to osmotic, pH, and shear stresses, we found that growth media pH values of 6.7 or higher did not support growth of two Sf9 variant cell lines (see FIG. 1). While adaptation of Sf9 may be possible, the parental Sf21 cell line was selected based on its survival and growth rate compared to the two tested Sf9 clones at the elevated pH levels tested.

EXAMPLE 4

Expression of CHIKV Polyprotein and VLPs in Sf21 Cells in Elevated pH Growth Medium It was previously described herein that cDNA encoding the CHIKV polyprotein could be expressed in insect cells under normal process conditions (pH in the 6.0-6.3 range), but no VLPs were formed (see EXAMPLE 2).

The intracellular pH of Sf21 cells remains at or near 7.0 in response to extracellular pH variation from 6.2 to 6.8, and is not affected by baculovirus infection (Medina et al. *Cytotechnology* 17: 21-26. (1995)). However, based on the slightly acidic nature of insect cell growth media and previously reported sensitivity of the CHIKV E1/E2 complex, which is a structurally important component of the target VLP, and *alphavirus* budding to extracellular pH (Akahata et al., 2012, supra, Lu et al. *J Virol* 75: 8329-8339 (2001)), the effects of elevated culture pH on cell surface display of CHIKV glycoproteins and on VLP production were examined. While strain 37997 VLP yield was not affected significantly by modulation of pH in the range of 7.0-7.9 when expressed in HEK293 cells ((Akahata et al., 2012, supra), the much lower pH 6.0-6.4 range of insect cell growth medium allowed for the possibility that increasing pH toward or into the typical mammalian cell culture pH range could be beneficial in this expression system.

Figure 2:
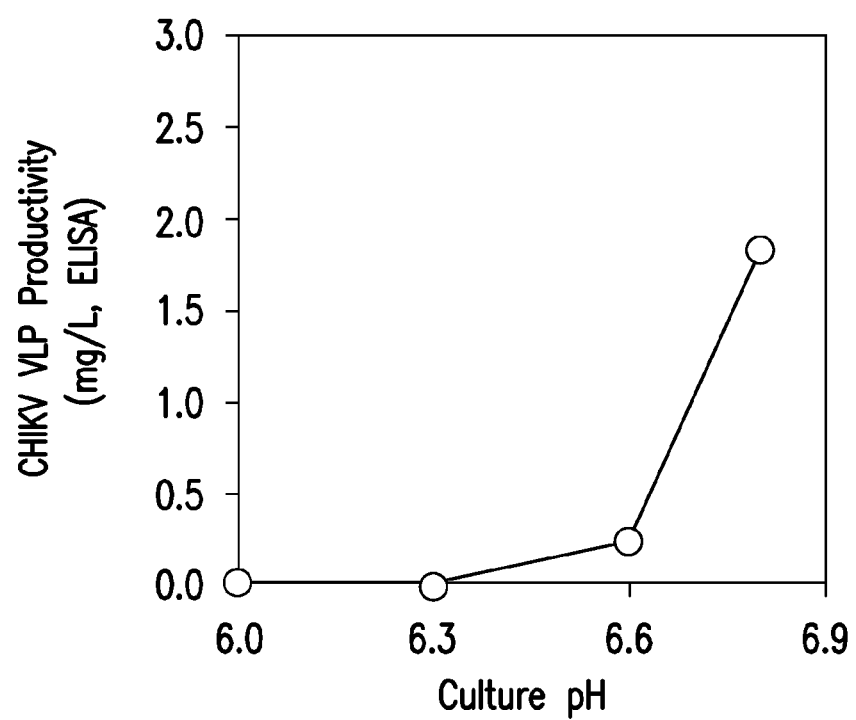
FIG. 2 shows the effect of culture pH on baculovirus-mediated production of CHIKV VLPs in Sf21 cell culture.

After selection of a suitably robust cell line as described in Example 3, a pH-ranging experiment was conducted as described below. This experiment demonstrated the production of budded recombinant CHIKV VLPs from baculovirus infected Sf21 cells (see FIG. 2). In addition to establishing production of detectable VLP levels at pH 6.6, productivity was found to significantly increase with further increase in pH.

Sf21 cells were grown in suspension culture in commercially available growth medium (Sf-900 II SFM, pH approximately 6.0-6.3) according to protocols well known in the art of insect cell culture. Cells were centrifuged gently to exchange the medium, and the cell pellet was re-suspended in standard range growth media (pH 6.0 and 6.3) and media which had been pre-adjusted upward to an elevated pH range (pH 6.6 and 6.8) by addition of sterile NaOH. For comparison to the native medium, pH 6.0 and 6.3 Sf900-II SFM were also included. These resulting cell cultures were then infected with a recombinant baculovirus carrying cDNA coding for the CHIKV structural polyprotein (UniProtKB/Swiss-Prot accession AAU43881.1) under control of the AcMNPV polyhedrin promoter. Cell density at infection ranged from 1.5-2.5 million viable cells/mL with a multiplicity of infection (MOI) of approximately 1.0 pfu/cell. Samples were removed from the baculovirus-infected cell cultures 4 days post-infection and then centrifuged to separate cells from supernatant. The cell pellet and clarified culture supernatant were subjected to Western Blot analysis and a sandwich ELISA, as described in EXAMPLE 1.

When Sf21 was infected with AcMNPV-CHIKV37997 in un-modified culture media at pH 6.3, mean fluorescence intensity (MFI) from cell surface immunofluorescence staining with neutralizing antibody m242 was observed to be only 4-fold greater than the negative control (NC) background and substantially lower than the HEK293 positive control transfection. No visible E2 band was detected by Western blot of Sf21 culture supernatants at pH 6.0-6.3, but a faint E1 antibody-reactive band was detected. However, no quantifiable qELISA signal was observed in this pH range, suggesting that the weak E1 signal by Western blot could have resulted from the release of low levels of intracellular E1 due to the lytic baculovirus infection process.

When culture pH was increased from 6.3 to 6.8, MFI from m242 surface staining of Sf21 increased to 22-fold over negative control background and became more similar in magnitude to transfected HEK293. Upon increase from pH 6.3 to pH 6.6 and 6.8, E1 and E2 bands were detected in increasing intensity by Western blot of Sf21 supernatants, and qELISA indicated the production of an increasing concentration of CHIKV VLPs. Despite these consistent increases with elevated culture pH, the E1 and E2 Western blot band intensities and qELISA signal for Sf21 at pH 6.8 still did not reach the same protein or VLP production levels as the HEK293 positive control. The increase in conformational E1/E2 complex detected on Sf21 cell surfaces and increase in budded VLP production as functions of culture pH suggest that stabilization of the E1/E2 complex may contribute to budding of CHIKV strain 37997 VLPs from baculovirus infected Sf21 cells.

Thus, as expected from the previous experiment, recombinant CHIKV protein bands were observed at the approximate expected molecular weight (E1, E2, and Capsid) by Western blot of all cell pellet lysates, regardless of culture pH. However, the ELISA result from culture supernatants was positive (signal greater than limit of quantitation) only at elevated pH (6.6 and 6.8) and ranged from 0.25-1.84 mg of VLP per liter of culture in this initial experiment. The increasing trend of VLP concentration as a function of culture media pH suggested further investigation of insect cell growth and recombinant protein production at pH>6.6 as a mechanism for increasing CHIKV VLP production.

Further enhancements in productivity were provided by growth medium re-formulation and adaptation of Sf21 to elevated pH conditions to generate a new cell line (see EXAMPLE 6).

EXAMPLE 5

Characterization of CHIK VLPs Produced in Sf21 Insect Cells

Figure 3A:
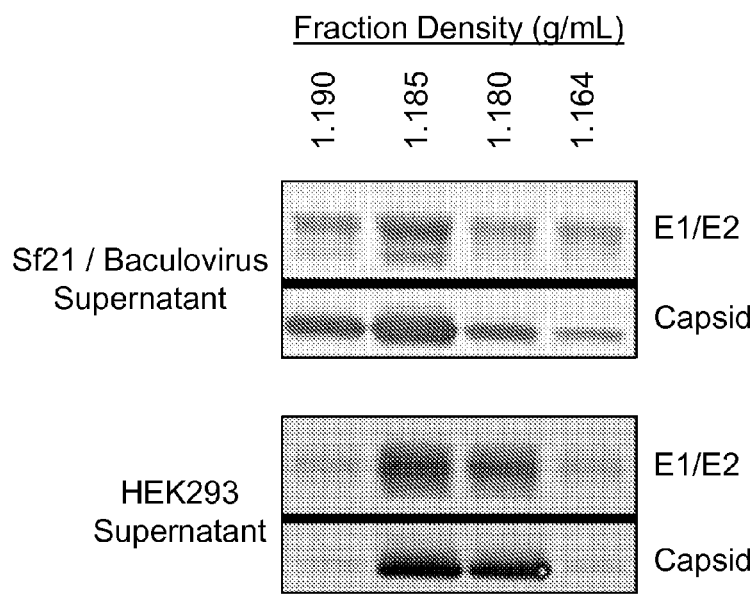
FIG. 3A shows density gradient ultracentrifugation fractions demonstrating co-localization of all 3 CHIKV structural proteins in the expected density range, as described in Example 2.
Figure 3B:
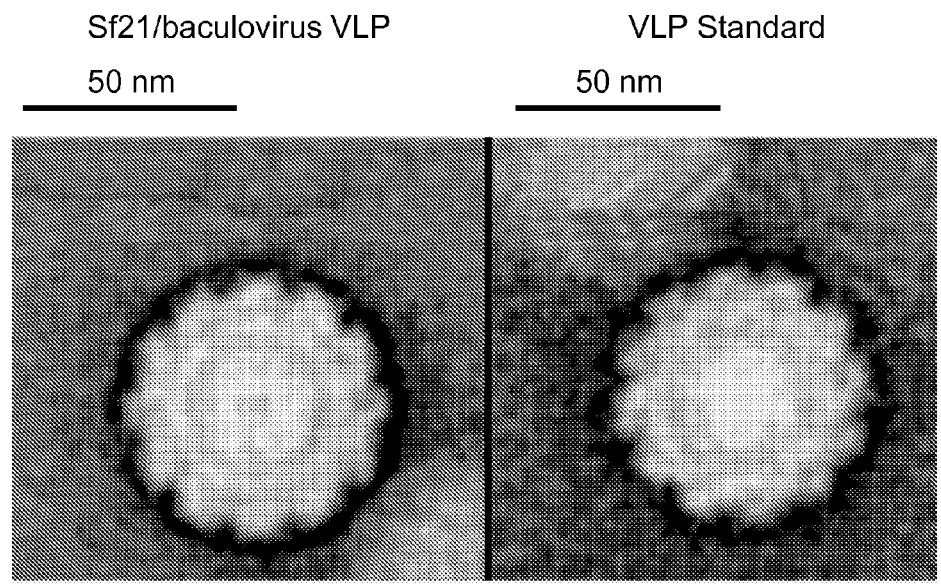
FIG. 3B provides transmission electron microscopy images comparing size and structure of recombinant CHIKV VLPs produced by elevated pH Sf21/baculovirus process and by the standard mammalian expression process in HEK-293 cells, as described in Example 2.

To determine if CHIKV VLPs produced in Sf21 cells at elevated pH were structurally correct, CHIKV VLPs were produced using the process described in Example 4. Supernatant samples were processed by equilibrium density gradient ultracentrifugation through a sucrose gradient and probed by Western Blot to establish the presence and density of VLPs by separating VLPs from un-assembled CHIKV proteins. The presence of intact VLPs in purified samples was also confirmed by TEM cryo imaging. The sample was preserved in vitrified ice supported by carbon films on 400-mesh copper grids. The sample was prepared by applying a 3 µL drop of sample suspension to a cleaned grid, blotting away with filter paper, and immediately proceeding with vitrification in liquid ethane. Both of these methods were used to confirm that VLPs produced by baculovirus infected insect cells at elevated pH are similar in physical size, density, and structure to those produced by the previously reported mammalian cell expression process (HEK293 cells, see FIGS. 3A and 3B).

EXAMPLE 6

Development of a pH-Adapted Insect Cell Line

In order to expand the range of culture conditions available for recombinant protein production in *Spodoptera fru-giperda* cells, Sf21 was adapted to grow robustly at an elevated culture pH range (7.0-7.4) relative to previous reports (hereinafter "MRK-SfBasic" cell line). Although CHIKV VLPs were produced from infected Sf21 cells and detected by qELISA at pH 6.6-6.8, this culture pH range is outside the reported optimum for Sf9 and Sf21 cell lines and is approaching the reported limit of normal physiology for cultured insect cells. Due to the heterogeneous nature of the Sf21 cell line (Vaughan et al. *In Vitro* 13: 213-217 (1977); Pasumarthy et al., *Biotechnol Prog* 10: 314-319 (1994)), it was hypothesized that applying pH stress by gradually increasing culture pH in a suitable growth medium over many passages could allow cells to adapt or be selected to produce CHIKV VLPs more effectively in an elevated culture pH range. Sf21 was selected as the parental cell line after subjecting several insect cell lines to high pH stress to determine their suitability for stress-based adaptation, as described in EXAMPLE 3.

Growth Medium Re-Formulation

Figure 4:
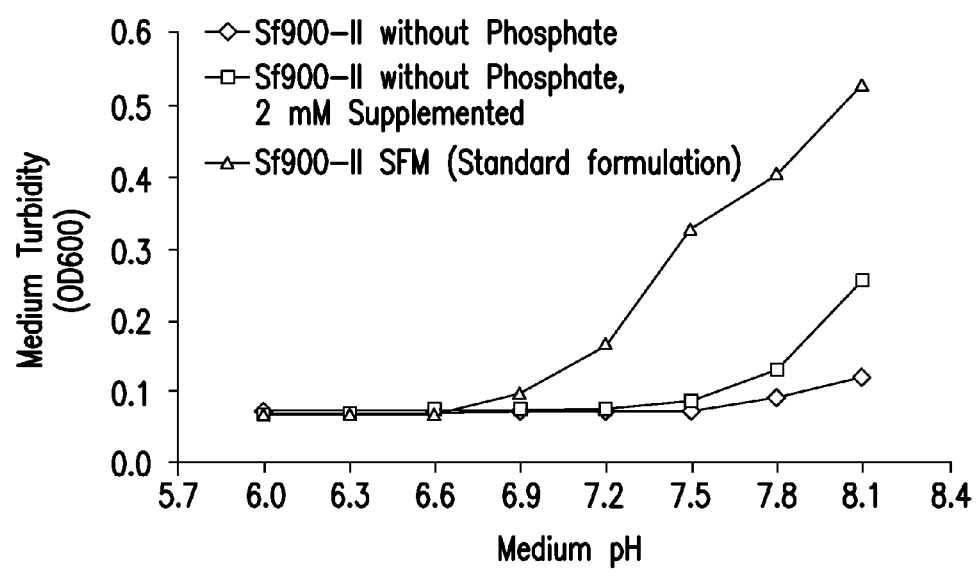
FIG. 4 shows the effect of phosphate concentration on the precipitation of media components from serum-free growth medium, as measured by optical density at 600 nm.

Both classical insect cell growth media (e.g. Grace's, TNM-FH, TC-100) and more recently developed serum-free media ("SFM", commercially available from Gibco/Invitrogen, BD Biosciences, Expression Systems LLC, Hyclone, Sigma-Aldrich, etc.) typically utilize phosphate in relatively high concentrations as the primary buffering agent (Richardson, C. D. (Ed.) *Methods in Molecular Biology* 39:65-202 (1995)). In contrast, mammalian cell culture media formulations typically utilize bicarbonate as the buffering agent, with lower levels of phosphate added to meet the phosphate needs of cell growth (Drugmand et al., *Biotechnology Advances* 30:1140-1157 (2012)). In addition to the reported biological limitation of lepidopteran insect cell culture to a pH range of 6.0-6.8, high-phosphate media do not support robust cell growth at elevated pH (>6.7) due at least in part to precipitation of media components (see FIG. 4) when the pH is adjusted in the presence of other required components (such as calcium). This issue was identified (<pH 6.8) as a barrier to testing elevated culture pH experimental conditions (Li et al., *Nature* 468:705-708 (2010)), leading investigator s to restrict testing to pH 6.8 to minimize the precipitation of media components.

To facilitate the adaptation of Sf21 to higher pH, two approaches were taken to formulate growth medium for culture of Sf21 at greater than 6.7-6.8. In one method, sterilizing grade 0.22 µm membrane filters and/or high speed centrifugation were used to remove media component precipitates after titration with a base such as NaOH. While sufficient to support initial investigation, this method is laborious to produce large volumes of medium, results in reduction of potentially useful media components by physical removal (i.e. filtered out), and produces a final medium which is unstable. Titrations to higher pH levels after filtration resulted in additional and progressively increasing precipitate formation, and refrigerated storage (2-8° C., standard conditions for media storage) also led to additional precipitation.

As an alternative, a commercially available SFM (Sf900-II SFM, from Gibco) was re-formulated with a reduced phosphate concentration and supplemented with a minimal insect salt solution (MISS) and alternative buffer (see Tables 1-3 below) to minimize the side effects of upward pH adjustment during the adaptation process. MISS was formulated with a non-phosphate organic buffer, N,N-Bis(2-hydroxyethyl)-2-aminoethanesulfonic acid (BES), to create BES-MISS supplement. BES-MISS was mixed with Sf-900 II SFM in various ratios to reduce phosphate buffer concentration and modify salt/nutrient concentrations from those present in the base medium. The BES-MISS additive was designed and modified as needed to be iso-osmolar (same osmolality) to the base growth medium to prevent the deleterious effects of significant osmolality variation on cells. These re-formulations allowed straightforward adjustment of growth medium to pH 7.0-7.4 without loss of media components, and also support robust, exponential cell growth and high culture viability for MRK-SfBasic in this elevated pH regime.

Sf-900 II SFM was also custom re-formulated by the manufacturer without phosphate species for use as a base medium. Salts/nutrients and non-phosphate buffers were then supplemented back into the base medium to enable the desired performance at elevated culture pH. The final medium was designed and modified as needed to prevent the deleterious effects of significant osmolality variation on cells. Osmolality is altered by the concentration of many species of ions and molecules in solution, and thus each species may need to be varied within the concentration ranges listed to compensate for increase/decrease in other components. Insect cells are typically grown in media with osmolality of 330-375 mOsm/kg (Vlak et al. (Ed.), *Insect Cell Cultures: Fundamental and Applied Aspects*, 1996.), but they can tolerate a much wider range as well (350-500 mOsm/kg, Olejnik et al., Effect of hyperosmolarity on recombinant protein productivity in baculovirus expression system. *J. Biotechnol.* 102: 291-300 (2003)).

TABLE 1

Adaptation Medium Formulation (BES-MISS Sf900-II)

| Component | Concentration |
|---|---|
| Sf900-II SFM (Base Medium)* | 50% v/v |
| BES Minimal Insect Salt Solution | 50% v/v |

*Sf900-II SFM contains approximately 12 mM phosphate (EnzChek Phosphate Assay Kit), and thus the above adaptation medium contains approximately 6 mM phosphate.

TABLE 2

BES Minimal Insect Salt Solution (MISS) Composition

| Component | Concentration |
|---|---|
| Sucrose | 123.5 mM |
| NaCl | 50 mM |
| KCl | 20 mM |
| $CaCl_2 \cdot 2H_2O$ | 3 mM |
| $MgSO_4 \cdot 7H_2O$ | 10 mM |
| Glucose | 5 mM |
| Pluronic F-68 | 0.1% w/v |
| BES | 50 mM |

TABLE 3

Final Medium Formulation

| Component | Concentration |
|---|---|
| Sf900-II without Phosphate | Base Medium |
| Sodium Phosphate | 2-6 mM |
| BES | 25 mM |
| Additional Buffer** | 10-40 mM |

**Additional buffers tested include 10-40 mM of Bis-Tris, HEPES, Tris, MOPS, TES, Tricine, Glycyl-glycine were found to work sufficiently well for this application, albeit to different levels. Bis-tris, HEPES, MOPS, Tricine and Glycyl-glycine performed slightly better than Tris and TES.

Cell Line Adaptation

The cell line was adapted using a known progressive weaning/supplementing process. Briefly: a continuous culture of Sf21 cells was exposed via medium exchange (gentle centrifugation and re-suspension) to a modified medium formulation with increased pH (Sf900 II SFM adjusted to pH 6.7 by addition of 1N NaOH) and allowed to equilibrate and adapt until suspension cell growth began to approach the normal 20-24 hour PDT of a control Sf21 culture in Sf-900II medium. During recovery, the pH-adjusted Sf-900II 166 BES-MISS medium was refreshed every 2-5 days to maintain adequate nutrient levels and prevent acidification of the medium due to cellular metabolic activity. After cell growth recovered to sufficient levels to continue, the resulting cells were exposed via medium exchange (gentle centrifugation and re-suspension) to a further step-change in medium formulation (further increased pH 7.0 BES-MISS Sf900 II), and then the equilibration and adaptation phase was repeated. This entire process was repeated over several months until the cells were growing robustly in the desired medium formulation (pH≥7.0) with stable growth characteristics similar to parental cell line growth in the original un-modified growth medium. After repeated passaging in the final medium formulation for stabilization, a cell bank with 7.5% v/v DMSO (cryoprotectant) was generated and transferred to a liquid nitrogen controlled temperature unit for long-term storage.

Some loss of culture viability and total cells was observed by trypan blue exclusion upon initial exposure of Sf21 to culture pH greater than 6.6, but a significant proportion of cells remained viable. This response suggests that SfBasic resulted from both immediate stress-based selection and longer term stress-induced adaptation or increased tolerance over time.

Passaging schedules during adaptation were adjusted as needed to keep the cell concentration between 0.1 million and 10 million viable cells/mL, typically diluting from 3-5 million down to 0.5-1 million viable cells/mL at each passage. While pH adaptation was originally induced in Gibco Sf900-II SFM media, similar commercially available serum-free growth media from Expression Systems LLC and BD Biosciences were also found to support equivalent cell growth when used as a base medium in the same fashion (data not shown).

Properties of the MRK-SfBasic Cell Line

The resulting MRK-SfBasic cell line has several properties which distinguish it from its parental Sf21 cell line. The average cell diameter is 3-4 μm larger than the parental cell line (18-19 μm, a 20-25% increase in cell diameter from parental Sf21 at 15 μm) and there is an approximate 2-fold increase in DNA content per cell (as measured by flow cytometry and fluorescence microscopy), corresponding to an 82% increase in cellular volume. This difference in the average cell diameter of the pH-adapted and parental cell populations was established by Vi-CELL XR microscopy image analysis and is statistically significant (Two-Sample T-Test of 12 independent samples each, $p<0.01$). Propidium iodide (PI) stained SfBasic cells also produced qualitatively higher PI signal intensities in traditional fluorescence microscopy images acquired at a fixed exposure time. When subjected to flow cytometry-based cell cycle analysis, SfBasic cells in G1-phase yielded a 1.9-fold increase in mean fluorescence intensity over the parental Sf21.

Figure 5:
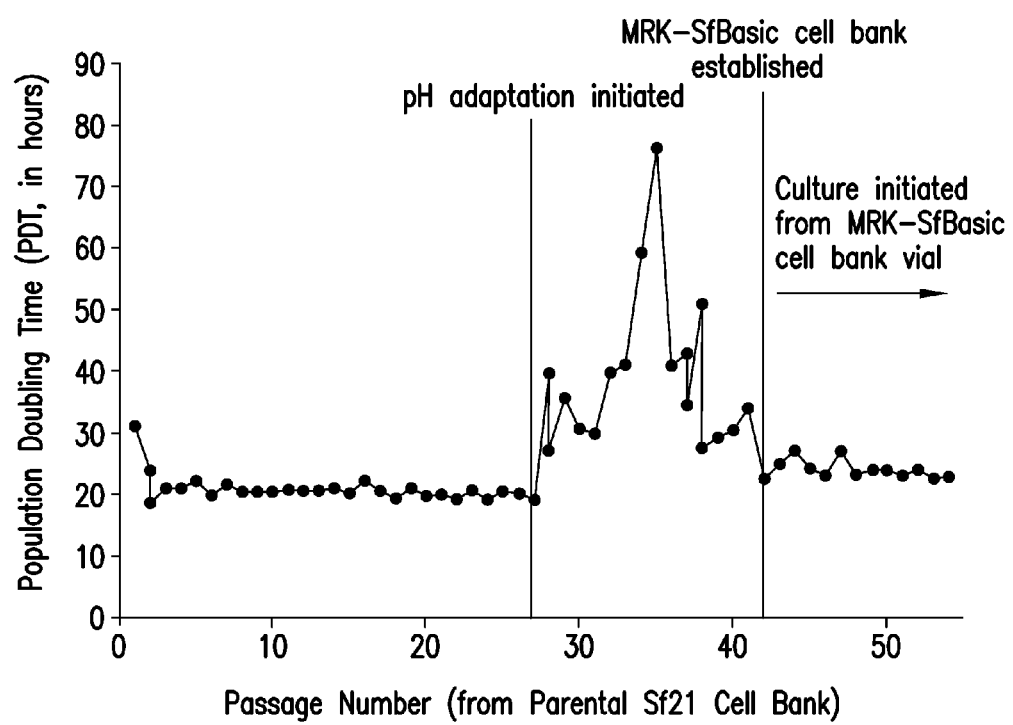
FIG. 5 provides the observed population doubling time for Sf21 cells prior to, during, and after pH adaptation process to generate MRK-SfBasic.

The PDT in pH 7.0 medium was similar to that of the parental Sf21 cell line cultured in standard Sf900-II SFM medium (see FIG. 5). These cell line characteristics have been demonstrated to be stable upon routine passage out to 46 passages (>2500 continuous culture hours, >100 population doublings) beyond the established MRK-SfBasic cell bank.

Figure 6:
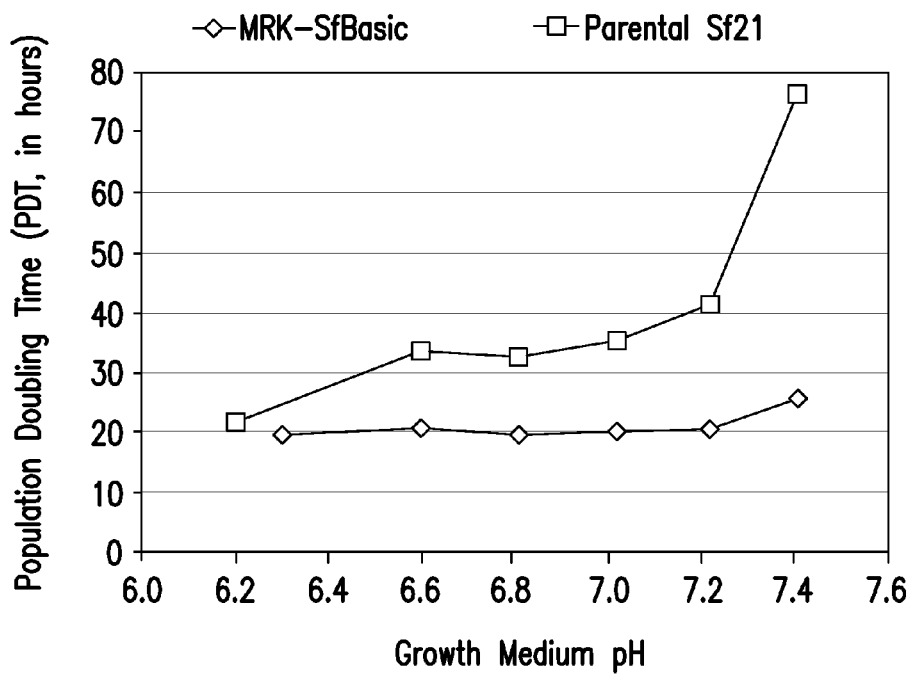
FIG. 6 shows the effect of growth medium pH on population doubling time for parental Sf21 and MRK-SfBasic cells.

The PDT of MRK-SfBasic cells was also compared to the PDT of parental Sf21 cells in several different growth media with varying pH (6.2-7.4). Results show that the MRK-SfBasic cell line grew robustly with a PDT of 20-30 hours from pH 6.3-7.4, whereas the parental Sf21 cells began to show signs of culture lag and depressed growth at pH 6.6 and displayed a significantly decreased growth rate in the pH 7.2-7.4 range (see FIG. 6 and Table 4).

The broadening of the normal growth range of SfBasic as a function of pH suggests that this cell population may be the result of an overall increase in tolerance to pH, as opposed to an adaptation shift to a new optimum. The average cell diameter, culture viability, and growth rate of SfBasic have currently been demonstrated to be stable for 30 passages (approximately 90 population doublings) after adaptation, and no observation of phenotypic instability has yet been observed during continuous passage.

TABLE 4

Population Doubling Time of MRK-SfBasic Cells

| | Population Doubling Time (PDT, hr) as a Function of Growth Medium pH | | | | | |
|---|---|---|---|---|---|---|
| | 6.2-6.3 | 6.6 | 6.8 | 7.0 | 7.2 | 7.4 |
| MRK-SfBasic | 20 | 21 | 19 | 20 | 20 | 25 |
| Parental Sf21 | 22 | 33 | 32 | 35 | 41 | 76 |

EXAMPLE 7

Production of CHIKV VLPs in MRK-SfBasic Cell Line

Baculovirus stocks were produced as described in Example 1. A recombinant baculovirus carrying cDNA coding for the CHIKV structural under control of the AcMNPV polyhedrin promoter was used to infect cultures of MRK-SfBasic and Sf21 parental cell lines. Several different experiments were performed in which CHIKV VLPs were produced using the BEVS in the MRK-SfBasic cell line. Cell densities at infection ranged from 0.5-5 million viable cells/mL, with multiplicity of infection (MOI) of approximately 0.003-3 pfu/cell for infection. The MRK-SfBasic cells were routinely cultured at pH 7.0. The cells were media exchanged into Sf900-II (pH 6.0-6.3) for infection with baculovirus, then after 24 hour infection period, media exchanged into pH 7.4 media (Sf900-II BES-MISS medium) for VLP production, with pH controlled >7.0 such that pH remained >7.0 throughout the process, despite slight acidification by cellular metabolism.

Figure 7:
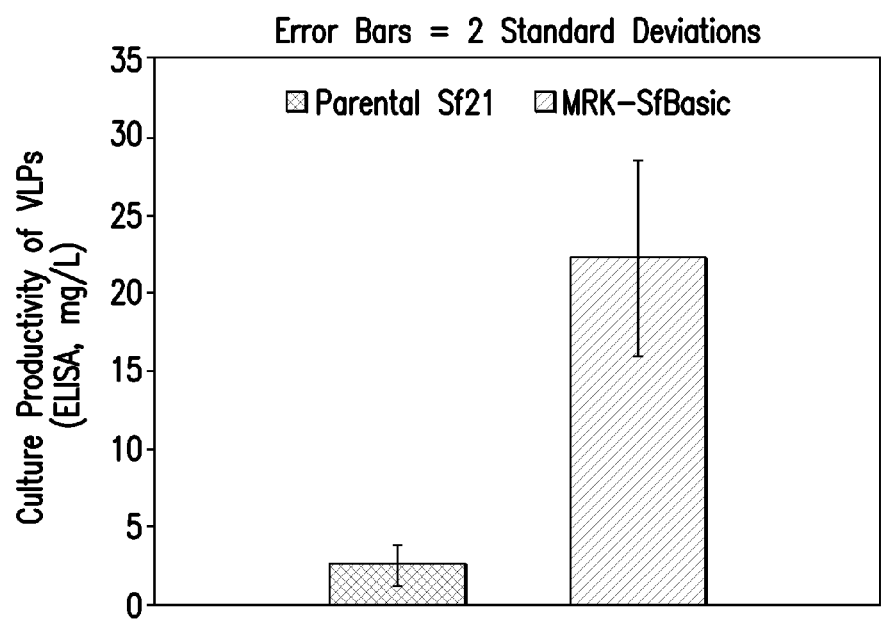
FIG. 7 shows the production of CHIKV VLPs in parental Sf21 and MRK-Sfbasic cells (ELISA, mg/L) via recombinant baculovirus infection in stirred tank bioreactors (see Example 7).
Figure 8:
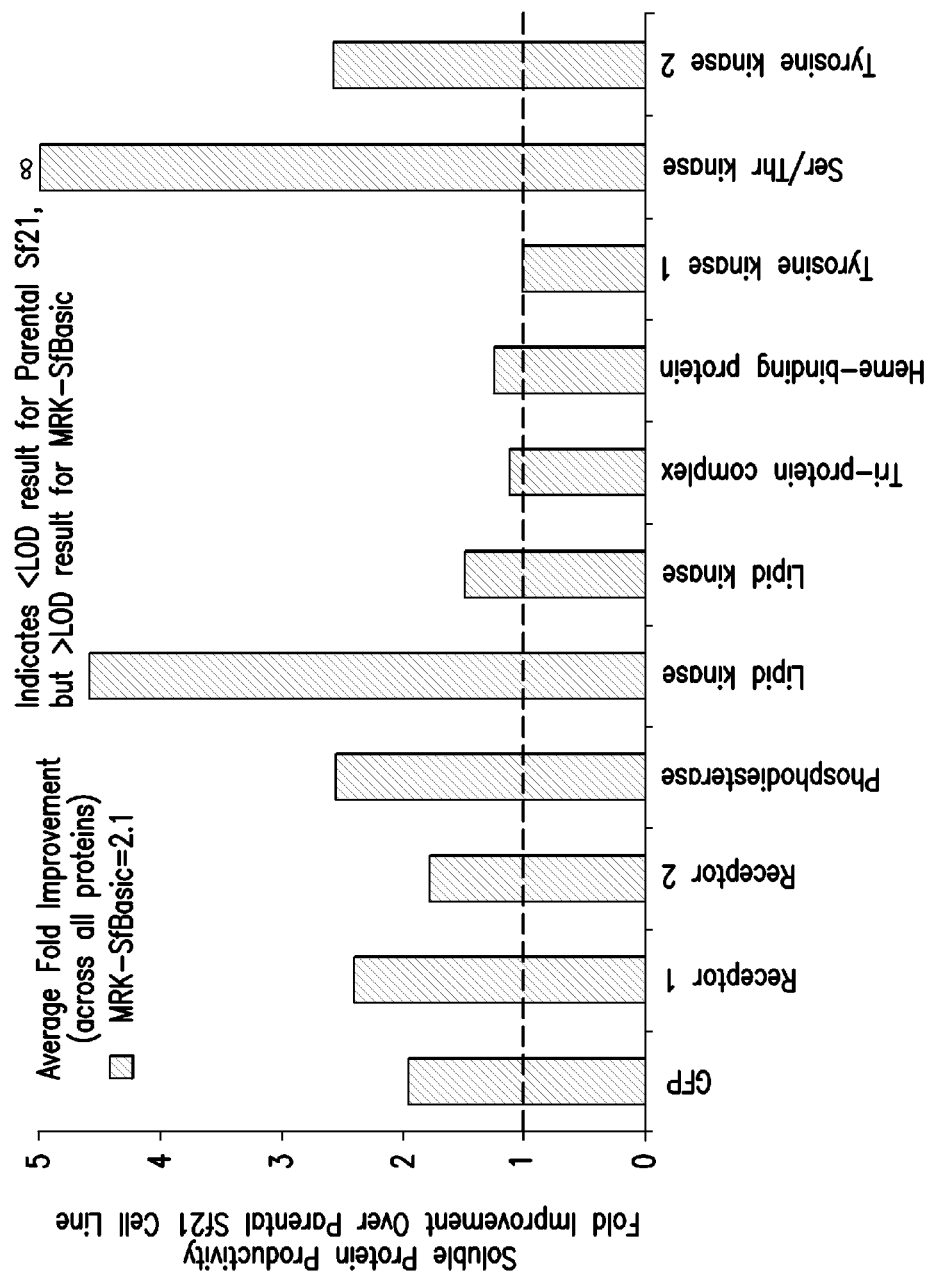
FIG. 8 shows the fold improvement of expression level of a GFP reporter protein and 10 randomly selected human targets from a variety of protein classes recombinantly produced in MRK-SfBasic cells compared to parental Sf21 cells.
Figure 9:
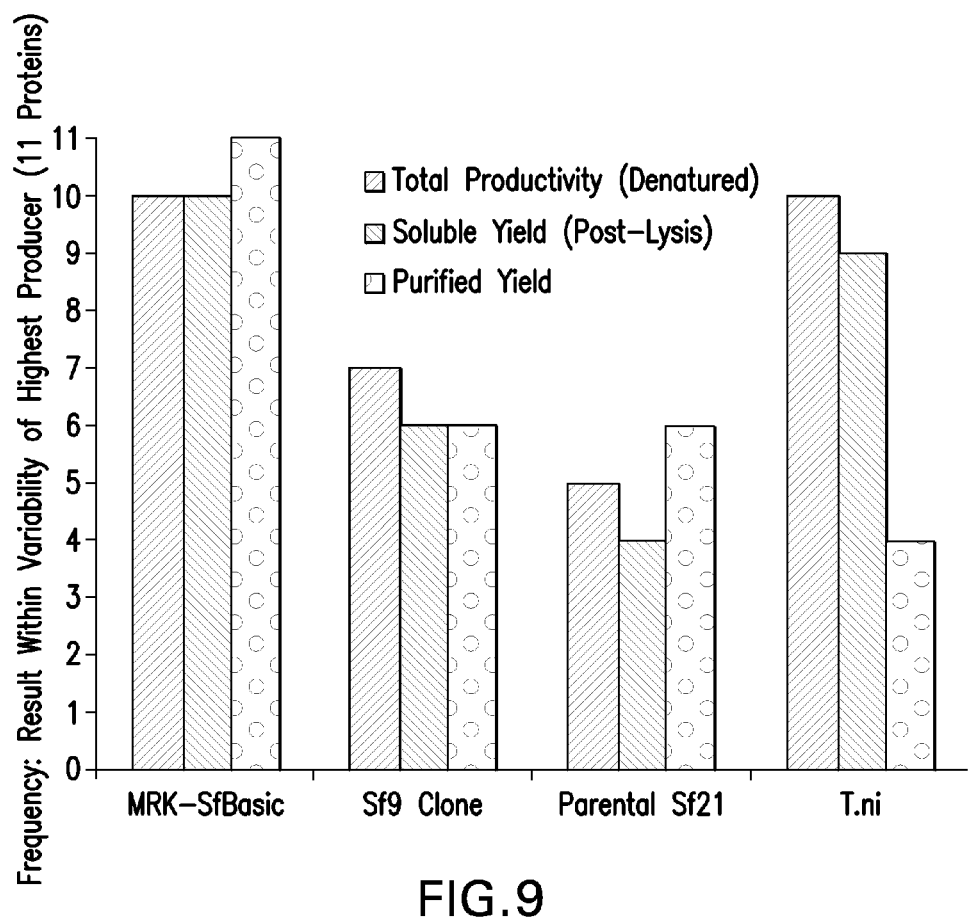
FIG. 9 shows the total productivity, soluble yield (post-lysis) and purified yield of best producing cell line for an 11-protein panel as measured throughout the production process; 1 frequency point for each protein yield within 2-fold of the best producing cell line for that target molecule, 0 for all other outcomes (11 point maximum, see Example 8).
Figure 10:
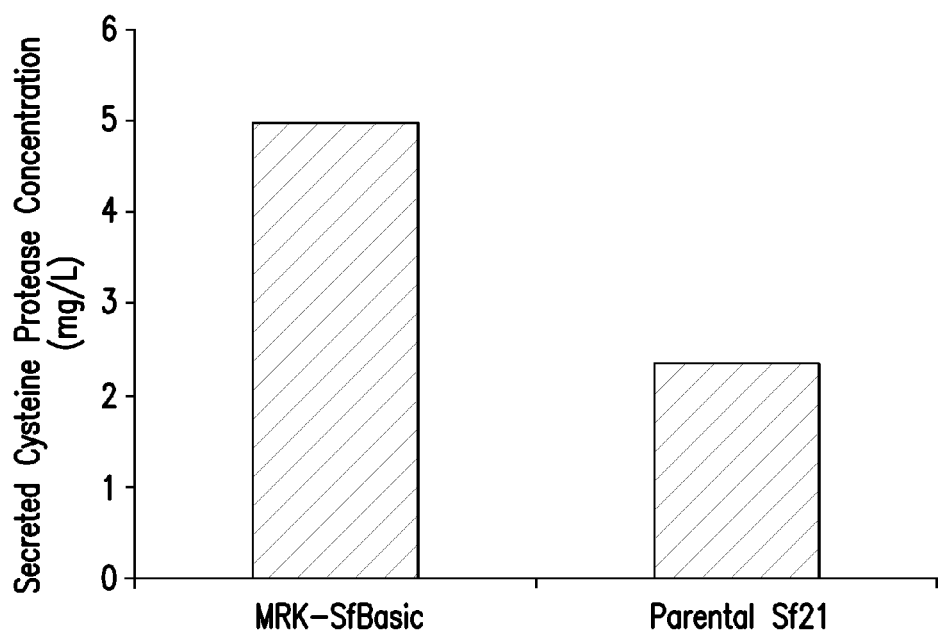
FIG. 10 shows the concentration (mg/L) of a secreted recombinant cysteine protease in the cell culture media of MRK-SfBasic and its parental Sf21 cell line (see Example 8).

Production and secretion of a recombinant CHIKV VLP containing these E1 and E2 proteins in their desired pre-fusion structural conformation was enhanced 9-fold in MRK-SfBasic compared to the parental Sf21 cell line (see FIG. 7). Production of VLPs in MRK-SfBasic was also accomplished by transient transfection using a DNA expression vector, whereas transfection of the parental Sf21 did not produce ELISA-detectable quantities of VLP (data not shown). When this production process was scaled up from small-scale shake flask infections into a larger shake flask and a stirred tank bioreactor, very similar CHIKV VLP productivities were achieved.

The optimized VLP production and scale-up of the SfBasic infection process supported chromatographic purification of large quantities of CHIKV VLPs. Purified VLPs from SfBasic had similar buoyant density to the HEK293-derived VLP standard when subjected to ucrose density gradient ultracentrifugation and Western blot detection. The 65.8±2.2 nm mean diameter of SfBasic-derived VLPs determined by dynamic light scattering (DLS) was not significantly different from the 63.7±2.4 nm mean diameter of the VLP standard (Two-Sample T-Test, p=0.19). 2D class averaging of electron micrograph images revealed that VLPs produced by SfBasic demonstrate slight differences in electron density compared to the VLP standard, but that the overall VLP size, icosahedral symmetry, and structure are very similar. After chromatographic purification from SfBasic culture, fractional counting of 422 particles in the electron microscopy images yielded a 97% CHIKV VLP fraction with 3% residual baculovirus by particle count. The SDS-PAGE protein purity for the final SfBasic-derived VLP preparation was 83%, the same purity as the HEK293-derived VLP standard lot used for comparison herein.

EXAMPLE 8

Expression of Multiple Reporter and Intracellular Proteins in MRK-SfBasic Cell Line Recombinant baculoviruses expressing a randomly selected panel of human protein targets (10 proteins, from various classes) or a reporter/model protein (Green fluorescent protein) were produced using standard molecular biology procedures well known in the art of baculovirus and insect cell expression; e.g. Bac-to-Bac site-specific transposition in *E. coli* or homologous recombination and plaque purification in insect cells. Lepidopteran insect cell lines (MRK-SfBasic, an Sf9 clone, parental Sf21, and *T. ni*) were maintained in continuous culture according to procedures well known in the art of insect cell culture.

Suspension cultures of insect cells (MRK-SfBasic, its parental Sf21, an Sf9 clone, and a *T. ni* cell line) were propagated in commercially available serum-free growth media using practices well known in the art. These cultures were infected with recombinant baculovirus at a fixed MOI and cell density (standard high-throughput screening process). Cell disruption was initiated 3 days post infection using a lysis buffer (25 mM Tris-HCl pH 8.0, 30% glycerol, 150 mM NaCl, 10 mM Imidazole, 50 units per mL of Benzonase), and target proteins were then captured and purified using affinity chromatography (HisSelect resin). Protein concentrations directly from cell culture (Total Productivity), immediately after lysis (Soluble Yield), and post-chromatography (Purified Yield) were determined by Western blot. All three sample concentrations were quantified by comparison to a standard curve using an anti-oligohistidine antibody and an oligohistidine-tagged protein standard of known concentration, and all productivities/yields were normalized to equivalent culture volume for comparison (i.e. microgram of target protein produced per milliliter of cell culture.

The results of BEVS expression of a panel of recombinant reporter and human intracellular proteins demonstrate that the MRK-SfBasic cell line produces a variety of non-glycoprotein targets at equivalent or elevated levels relative to the parental Sf21 line (see FIG. 8). This indicates that the pH-stress based adaptation has resulted in an altered cell population in MRK-SfBasic which has overall improved characteristics and utility for recombinant protein production across a broad range of target molecules.

MRK-SfBasic intracellular productivity also compared favorably to an Sf9 clone and a suspension *Trichoplusia ni* cell line, with top ranking recombinant protein yields for 10-11 of the same 11 targets across 3 process intermediates (see FIG. 9). Production and secretion of a recombinant cysteine protease also increased by approximately 2-fold in MRK-SfBasic relative to its parental Sf21 cell line (see FIG. 10.)

EXAMPLE 9

Immunogenicity of Baculovirus-Derived CHIKV VLPs

Figure 11A:
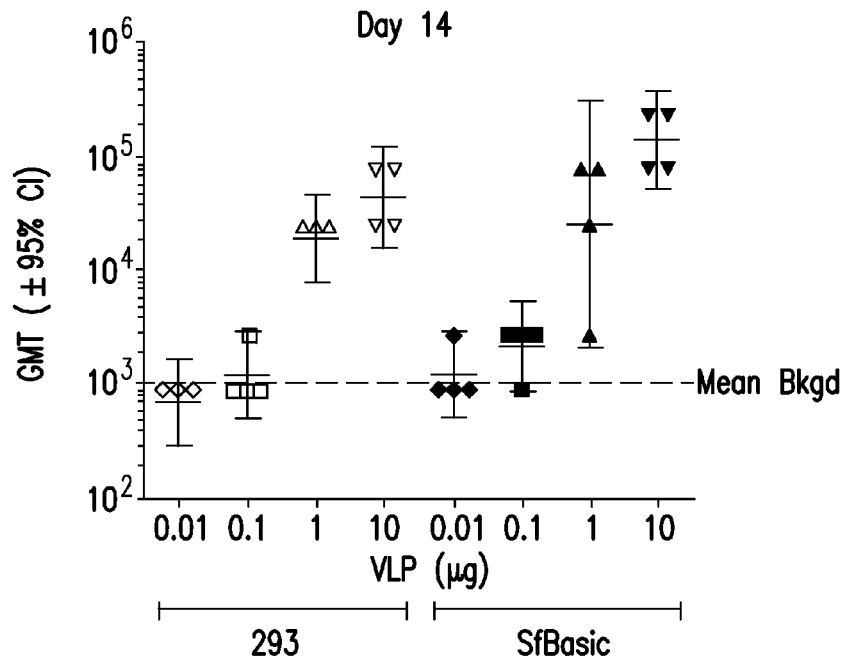
FIG. 11 compares the immunogenicity of MRK-SfBasic/baculovirus-derived VLPs compared to 293-derived VLPs determined using a standard ELISA format. Shown are the antigen binding IgG concentrations for guinea pigs vaccinated with different dosages of VLPs (0.01, 0.10, 1.0 and 10 mg) derived from MRK-SfBasic or 293 cells immediately following a second dose of VLPs (day 14, panel A) or 7 days after the second dose (day 21, panel B) (see Example 9).
Figure 11B:
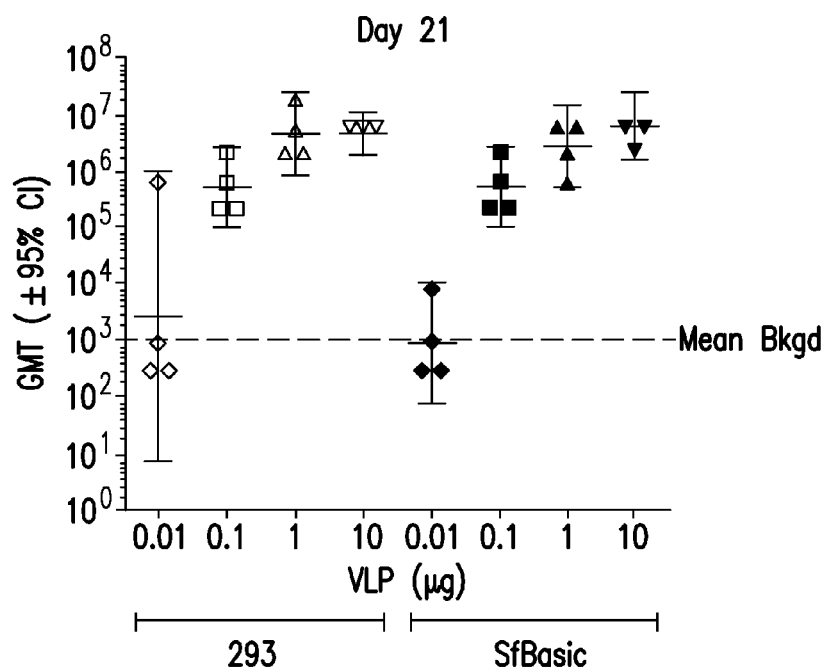

Purified preparations of CHIKV VLPs derived from transient transfection of HEK293 (control) and from elevated pH baculovirus infection of MRK-SfBasic were adjuvanted onto Adjuphos™ and then guinea pigs (N=4/group) were vaccinated IM with doses of 0.01, 0.10, 1.0, or 10 micrograms of VLP (as measured by sandwich ELISA). The animals were vaccinated at day 0 and day 14, and bled on days 14 and 21. Endpoint IgG titers were determined by immobilizing highly purified CHIKV VLPs (derived from HEK293 transient transfections) and determining antigen binding IgG concentrations using a standard ELISA format. The data indicate that MRK-SfBasic derived VLPs are non-inferior to HEK293 derived VLPs in eliciting an IgG response (FIGS. 11A and 11B).

Figure 12A:
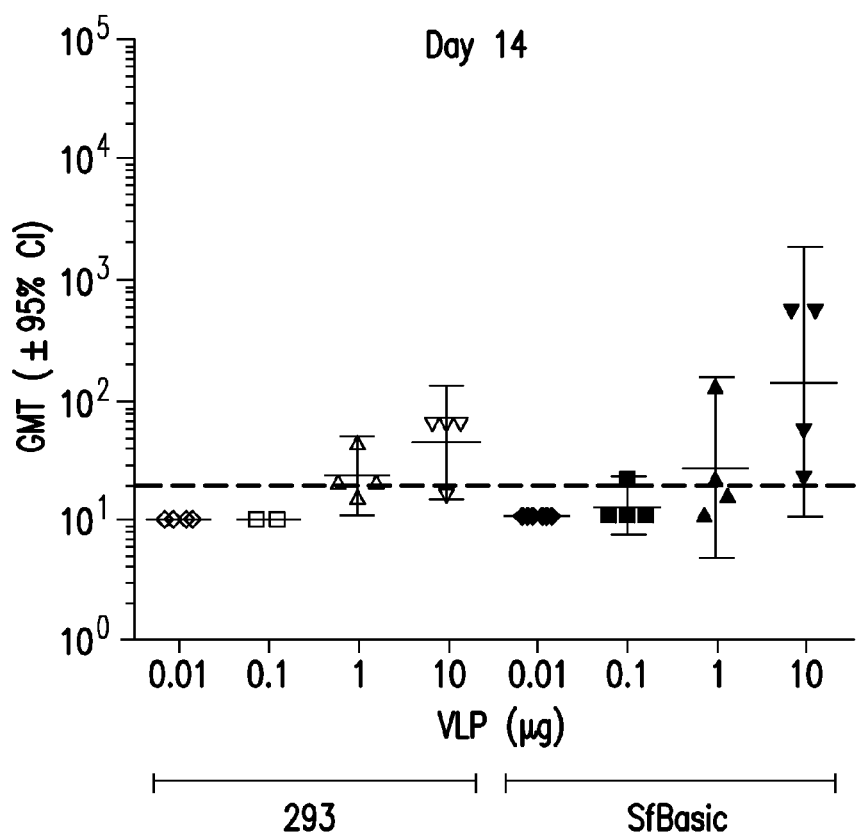
FIG. 12 provides the neutralizing antibody titers for the vaccinated guinea pigs described in Example 9 (see also FIG. 11). Shown are the neutralizing antibody titers for guinea pigs vaccinated with different dosages of VLPs (0.01, 0.10, 1.0 and 10 mg) derived from MRK-SfBasic or 293 cells immediately following a second dose of VLPs (day 14, panel A) or 7 days after the second dose (day 21, panel B) (see Example 9).
Figure 12B:
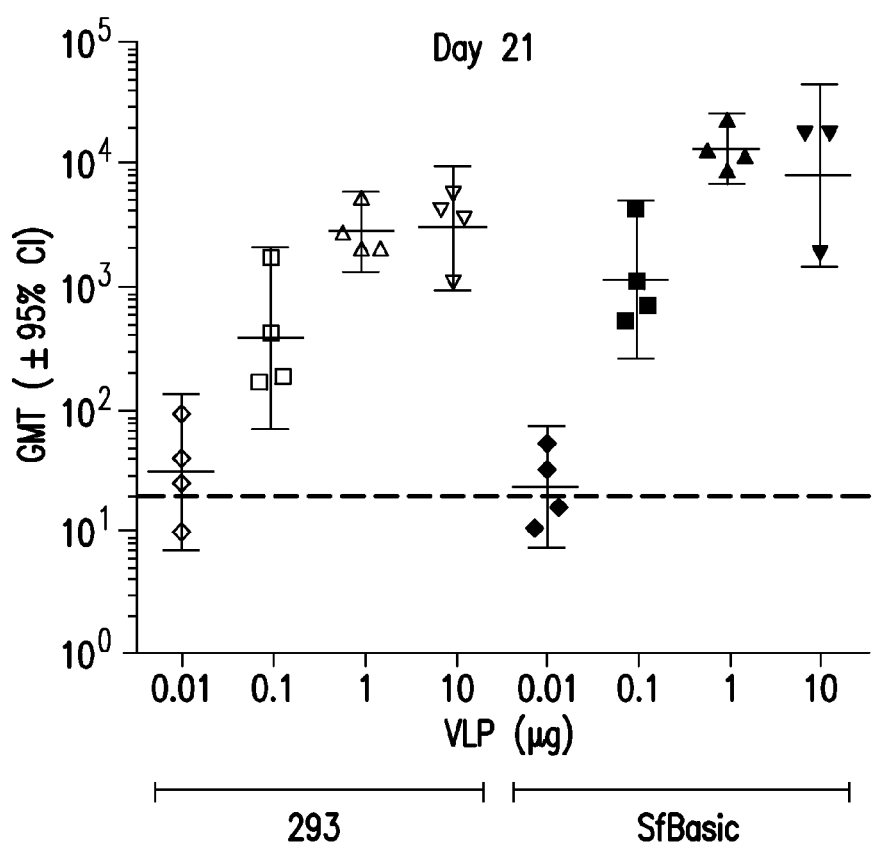
Figures 13A, 13B:
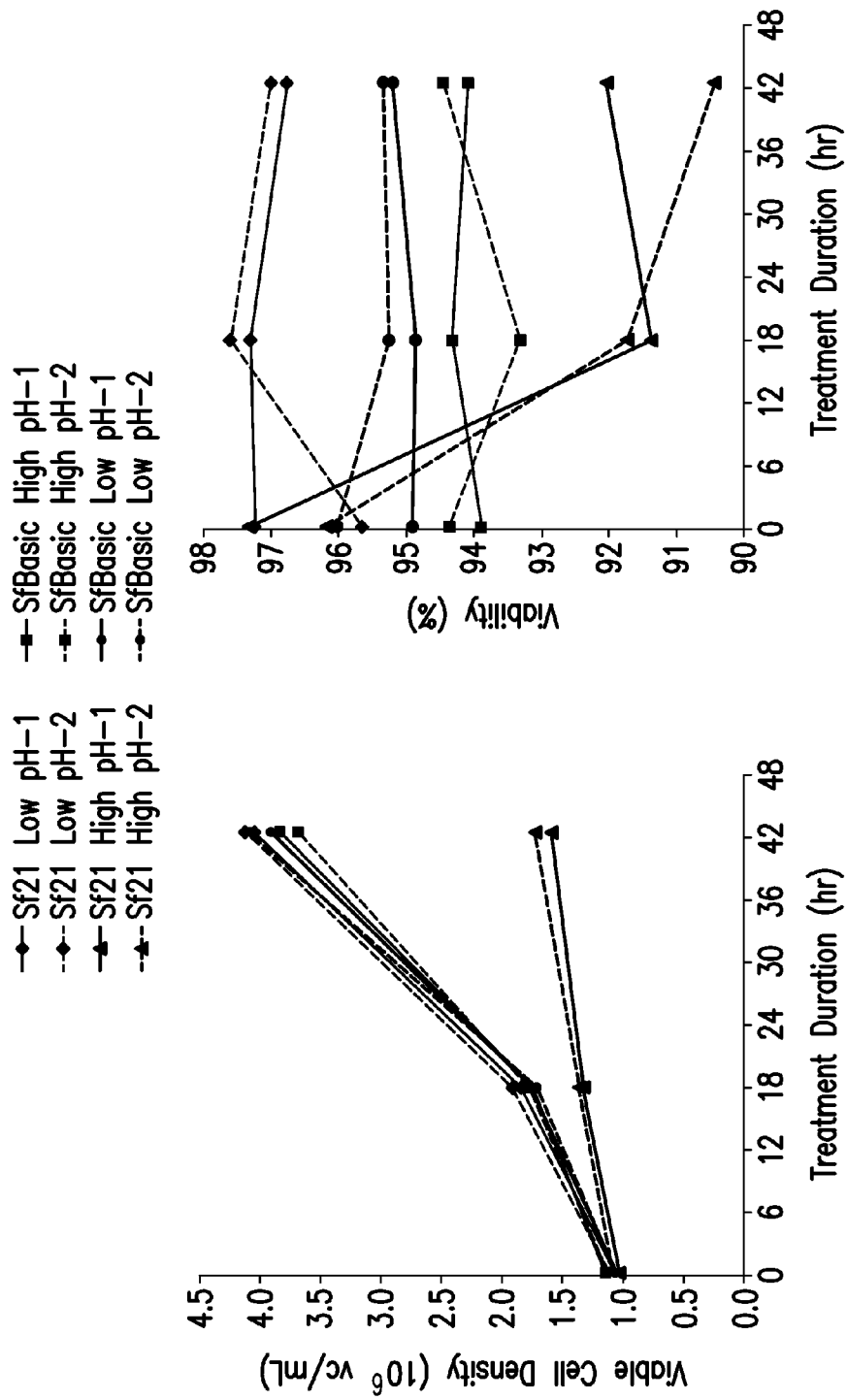
FIG. 13 provides the viable cell concentration and viable cell fraction observed upon treatment of Sf21 and MRK-SfBasic in low pH Sf-900 II SFM (pH 6.2) and high pH BES-MISS Sf900-II (pH 7.2) growth media (see Example 10). Numeric suffixes indicate duplicate experimental treatments.

To determine whether neutralizing antibodies were elicited in response to vaccination with CHIKV VLPs produced with the MRK-SfBasic cell line, neutralization titers were determined by mixing serially diluted guinea pig sera with 350 plaque forming units (PFU) of Chikungunya vaccine strain 181/25 (originally developed by the United States Army Medical Research Institute of Infectious Diseases, USAMRIID). After a one hour incubation, samples were added to Vero cell monolayers and incubated for 3 days. Vero cell monolayers were subsequently fixed and stained to visualize any disruption of the cell layer due to viral infection. Neutralization titers were determined by taking the reciprocal of the last serum serial dilution where the complete Vero cell monolayer remained visually intact (i.e. 100% neutralization). The data indicate that MRK-SfBasic derived VLPs are non-inferior to HEK293 derived VLPs in eliciting a neutralizing antibody response (FIGS. 12A and 12B).

EXAMPLE 10

Cell Concentrations of pH-Adapted and Parental Sf21 Cells under Different pH Conditions MRK-SfBasic and Sf21 cell bank vials were thawed and cultivated in suspension in BES-MISS Sf900-II (pH 7.2) and Sf-900 II SFM (pH 6.2), respectively. Cell suspension samples were removed and centrifuged to gently pellet the cells, and all growth medium was removed. In duplicate, the growth media for MRK-SfBasic and Sf21 were exchanged for BES-MISS Sf900-II (pH 7.2) and Sf-900 II SFM (pH 6.2) to generate a "High pH" and "Low pH" treatment for each cell line. Cell counts and cell viability were established microscopically using the Beckman Vi-CELL XR cell counter, trypan blue exclusion reagent, and image analysis software. MRK-SfBasic at both high and low pH was observed to reach similar cell concentrations to Sf21 in low pH conditions, whereas the cell concentrations for Sf21 at high pH were significantly reduced. A drop in the viable cell fraction was also observed for Sf21 in high pH media.

What is claimed is:

1. A method for the generation of an elevated pH-tolerant lepidopteran insect cells comprising:
   (a) culturing a population of cells from a lepidopteran insect cell line in a standard culture medium that supports the growth of insect cells and has a pH of from about 6.0 to about 6.4;
   (b) culturing the cells in elevated pH culture medium that has a pH that is greater than the pH of the standard culture medium in step (a); and
   (c) allowing the cells to adapt to the elevated pH culture medium, wherein the adapted cells exhibit similar growth characteristics at a pH greater than or equal to 7.0 to a population of cells of the insect cell line cultured in the standard culture medium.

2. The method of claim 1, wherein steps (b) and (c) are repeated one or more times, using an elevated pH culture medium with a pH that is progressively higher each time.

3. The method of claim 1, further comprising establishing a cell bank to produce a cell line.

4. The method of claim 1, wherein the pH of the elevated pH culture medium in step (b) is from about 6.5 to about 7.0.

5. The method of claim 1, wherein the pH of the elevated pH culture medium in step (b) is from about 7.0 to about 7.4.

6. The method of claim 1, wherein the elevated pH culture medium comprises less than 20 mM phosphate.

7. The method of claim 6, wherein the elevated pH culture medium comprises from about 0.1 to about 6 mM phosphate.

8. The method of claim 1, wherein the insect cell line of step (a) is an Sf9, Sf 21 or *Trichoplusia ni* cell line.

9. The method of claim 8, wherein the insect cell line of step (a) is Sf21.

10. An insect cell line produced by the method of claim 1.

11. A method for the recombinant production of a protein comprising:
    (a) transfecting a population of insect cells from a cell line produced by the method of claim 1 with a vector comprising a sequence of nucleotides that encodes the protein;
    (b) culturing the insect cells in culture medium with a pH from about 6.5 to about 7.8 under conditions that permit expression of the protein; and
    (c) optionally purifying the protein from the culture medium.

12. The method of claim 11, wherein the protein is a viral protein from a virus family selected from togaviridae, rhabdoviridae, herpesviridae, and flaviviridae.

13. The method of claim 11, wherein the vector is a baculovirus vector.

14. A culture medium for culturing insect cells at an elevated pH comprising a base medium capable of supporting the growth of insect cells, and about 20 mM or less phosphate, wherein the pH of the pH-tolerant medium is from about 6.8 to about 7.8, wherein the phosphate concentration is from about 0.1 mM to about 6.0 mM.

15. The culture medium of claim 14, wherein the medium comprises sodium, potassium, magnesium, calcium, and a carbon source.

16. The culture medium of claim 15, wherein the medium further comprises one or more of a non-ionic osmolality adjustment compound, a sheer protectant, and a buffer.

17. The culture medium of claim 14, wherein the medium comprises: from about 5 mM to about 200 mM sucrose, from about 5 mM to about 100 mM NaCl, from about 5 mM to about 75 mM KCl, from about 5 to about 25 mM $CaCl_2.2H_2O$, from about 5 to about 25 mM $MgSO_4.2H_2O$, from about 5 mM to about 50 mM glucose, up to about 1% w/v Pluronic F-68 and from about 5 mM to about 75 mM BES.

18. A pH-adapted lepidopteran insect cell line, wherein the cell line is derived from parental cell line Sf21 and possesses the properties of increased average cell diameter, increased DNA content per cell, and increased growth rate in elevated pH culture medium relative to the parental Sf21 cell line.

19. The pH-adapted insect cell line of claim 18, wherein the average cell diameter is about 2 to about 5 μm increased, and the DNA content per cell is about 1.5 to about 3-fold increased relative to parental Sf21, and the increased growth rate is in pH culture medium of about 6.8 to about 7.4.

* * * * *